US010155079B2

(12) United States Patent
Takahashi et al.

(10) Patent No.: US 10,155,079 B2
(45) Date of Patent: Dec. 18, 2018

(54) BLOOD TREATMENT FILTER DEVICE, PRIMING METHOD, AND BLOOD TREATMENT METHOD

(71) Applicant: Nipro Corporation, Osaka (JP)

(72) Inventors: Toshinari Takahashi, Osaka (JP); Masashi Yokota, Osaka (JP); Hiroshi Fukushima, Osaka (JP); Kimihiko Nakamura, Osaka (JP)

(73) Assignee: Nipro Corporation, Osaka (JP)

( * ) Notice: Subject to any disclaimer, the term of this patent is extended or adjusted under 35 U.S.C. 154(b) by 78 days.

(21) Appl. No.: 15/111,843

(22) PCT Filed: Jan. 20, 2015

(86) PCT No.: PCT/JP2015/051337
§ 371 (c)(1),
(2) Date: Jul. 15, 2016

(87) PCT Pub. No.: WO2015/111565
PCT Pub. Date: Jul. 30, 2015

(65) Prior Publication Data
US 2016/0339161 A1 Nov. 24, 2016

(30) Foreign Application Priority Data

Jan. 22, 2014 (JP) .................................. 2014-009058
Jan. 23, 2014 (JP) .................................. 2014-010214

(51) Int. Cl.
*A61M 1/16* (2006.01)
*A61M 39/22* (2006.01)
(Continued)

(52) U.S. Cl.
CPC ........ *A61M 1/1631* (2014.02); *A61M 1/3643* (2013.01); *A61M 39/22* (2013.01);
(Continued)

(58) Field of Classification Search
CPC .............. A61M 1/1631; A61M 1/3496; A61M 1/3633; A61M 1/3643; A61M 2205/3331;
(Continued)

(56) References Cited

U.S. PATENT DOCUMENTS 6,699,388 B1 3/2004 Iwamoto et al.
2009/0211985 A1 8/2009 Gulati et al.

FOREIGN PATENT DOCUMENTS

EP 1080741 3/2001
JP 2007236564 A 9/2007
(Continued)

OTHER PUBLICATIONS

European patent application No. 15740407.0, Extended European Search Report, dated Nov. 23, 2017.
(Continued)

*Primary Examiner* — Dirk R Bass
(74) *Attorney, Agent, or Firm* — Marshall, Gerstein & Borun LLP

(57) ABSTRACT

To provide a blood treatment filter device capable of efficiently utilizing a blood treatment filter.
A blood treatment filter device 20 has a filter sheet 26 through which a specific component among components forming blood is harder to pass than other components and a spacer sheet 27 through which the specific component is easier to pass than through the filter sheet 26. The filter sheet 26 has filter through-holes 39 disposed at intervals. The filter sheet 26 and the spacer sheet 27 are spirally wound in an overlapped state. The filter device 20 has seals 31 sealing both end portions in the longitudinal direction of a wound body 25 formed by the filter sheet 26 and the spacer sheet 27 which are spirally wound in a fluid-tight manner. The outer peripheral surface of the wound body 25 is formed by the filter sheet 26.

12 Claims, 14 Drawing Sheets

(51) Int. Cl.
   *A61M 1/36* (2006.01)
   *B01D 63/10* (2006.01)
   *B01D 65/08* (2006.01)
   *B01D 29/21* (2006.01)
   *A61M 1/34* (2006.01)

(52) U.S. Cl.
   CPC .............. *B01D 63/10* (2013.01); *B01D 65/08* (2013.01); *A61M 1/3496* (2013.01); *A61M 1/3633* (2013.01); *A61M 2205/3331* (2013.01); *A61M 2205/7563* (2013.01); *B01D 29/216* (2013.01); *B01D 2313/083* (2013.01); *B01D 2313/143* (2013.01); *B01D 2313/18* (2013.01)

(58) Field of Classification Search
   CPC .......... A61M 2205/7563; A61M 39/22; B01D 2313/083; B01D 2313/143; B01D 2313/18; B01D 29/216; B01D 63/10; B01D 65/08
   See application file for complete search history.

(56) References Cited

FOREIGN PATENT DOCUMENTS

| | | |
|---|---|---|
| JP | 4190150 B2 | 12/2008 |
| JP | 2010125208 A | 6/2010 |
| JP | 5164241 B2 | 3/2013 |

OTHER PUBLICATIONS

International Search Report (English translation), International Application No. PCT/JP2015/051337, dated Apr. 21, 2015.

[FIG. 1]
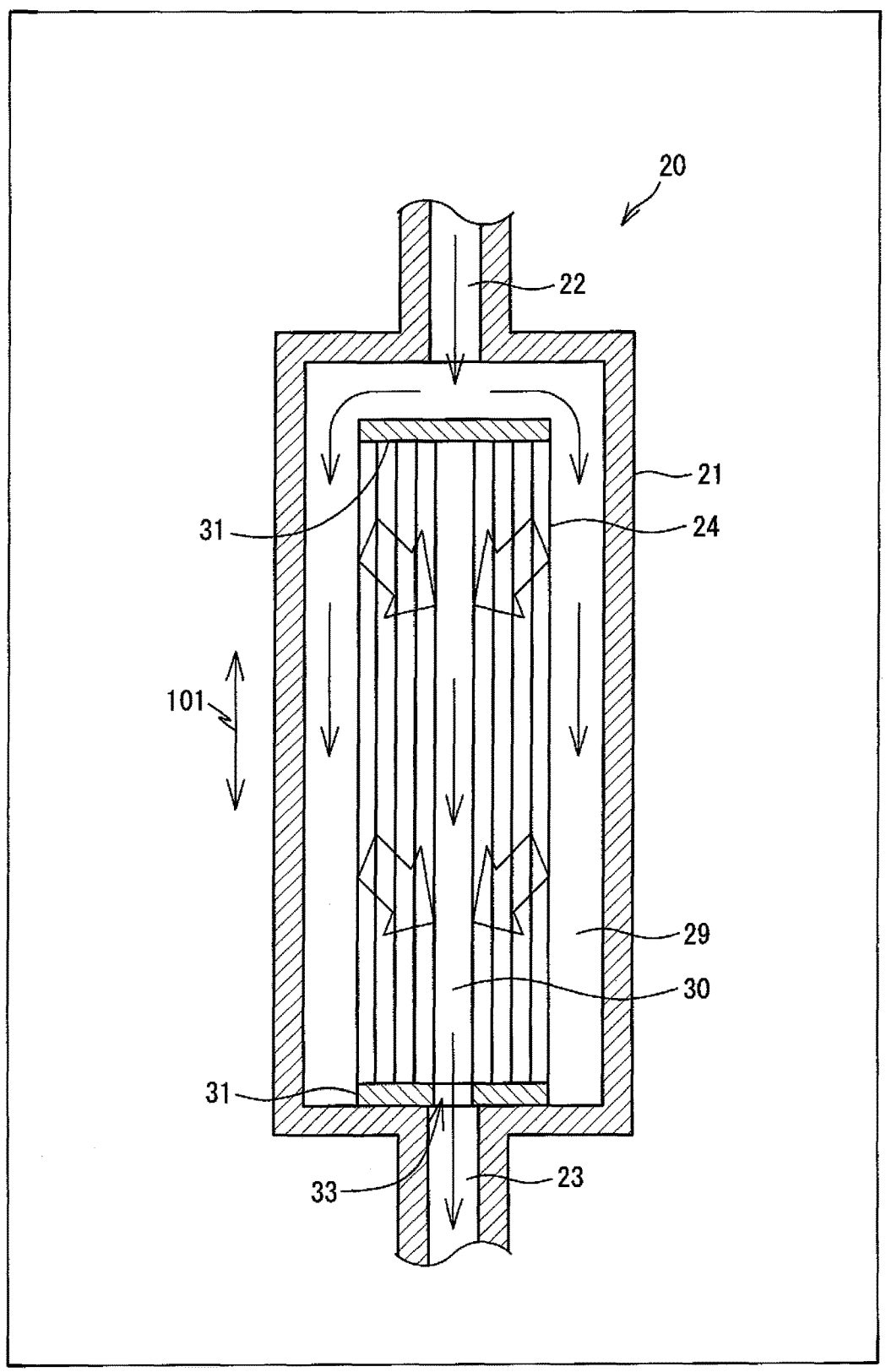

[FIG. 2]
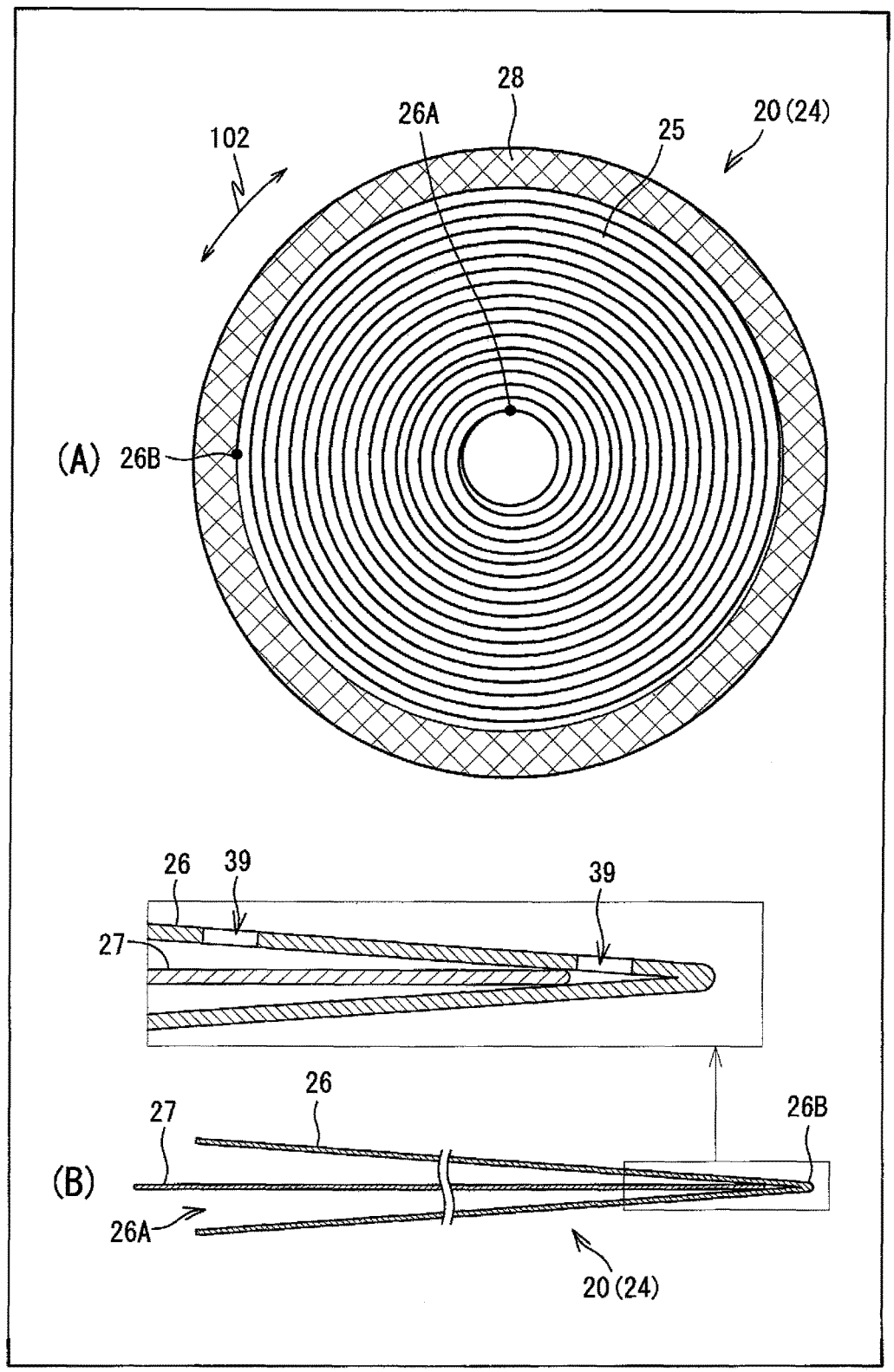

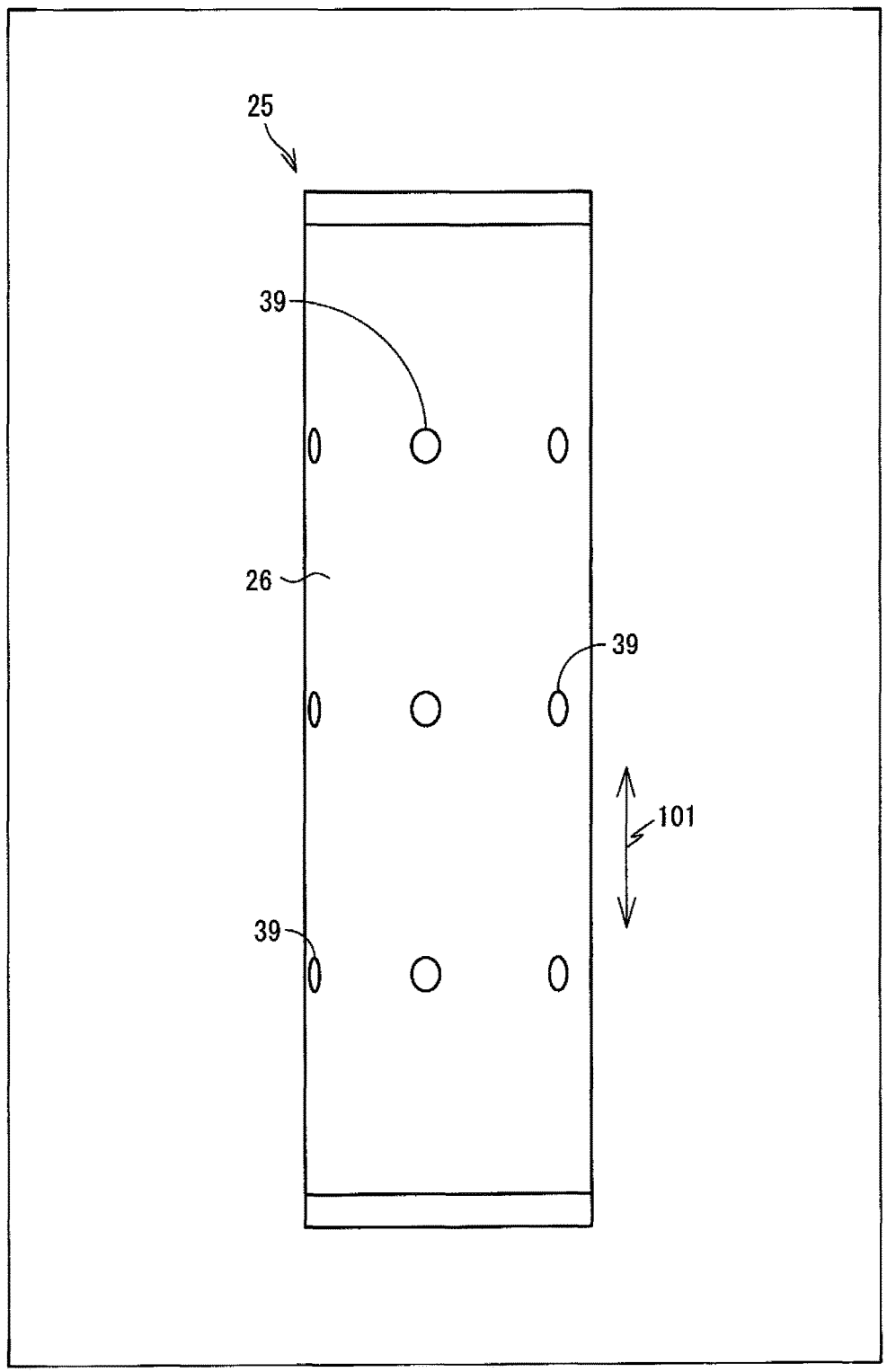
[FIG. 3]

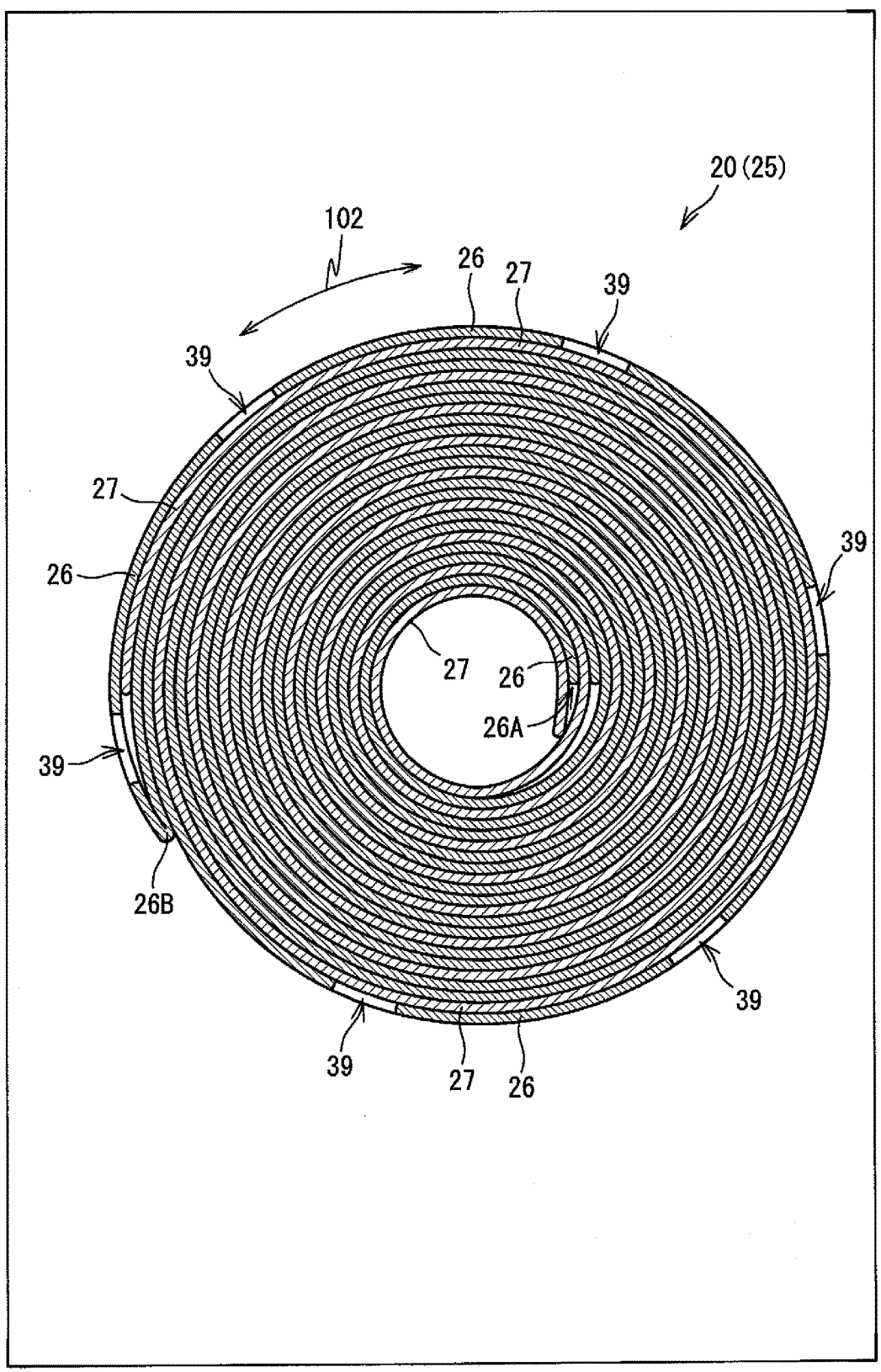
[FIG. 4]

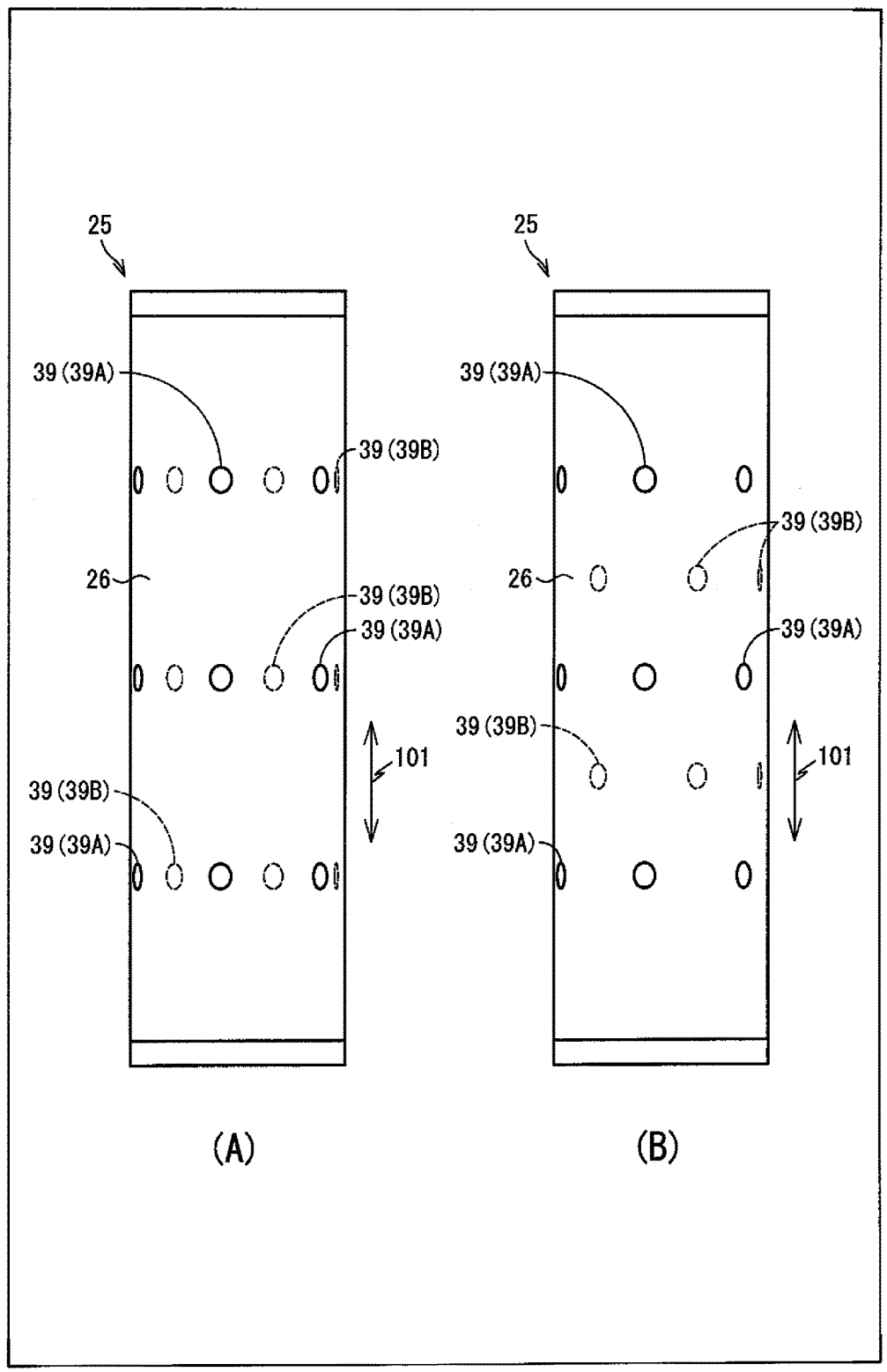
[FIG. 5]

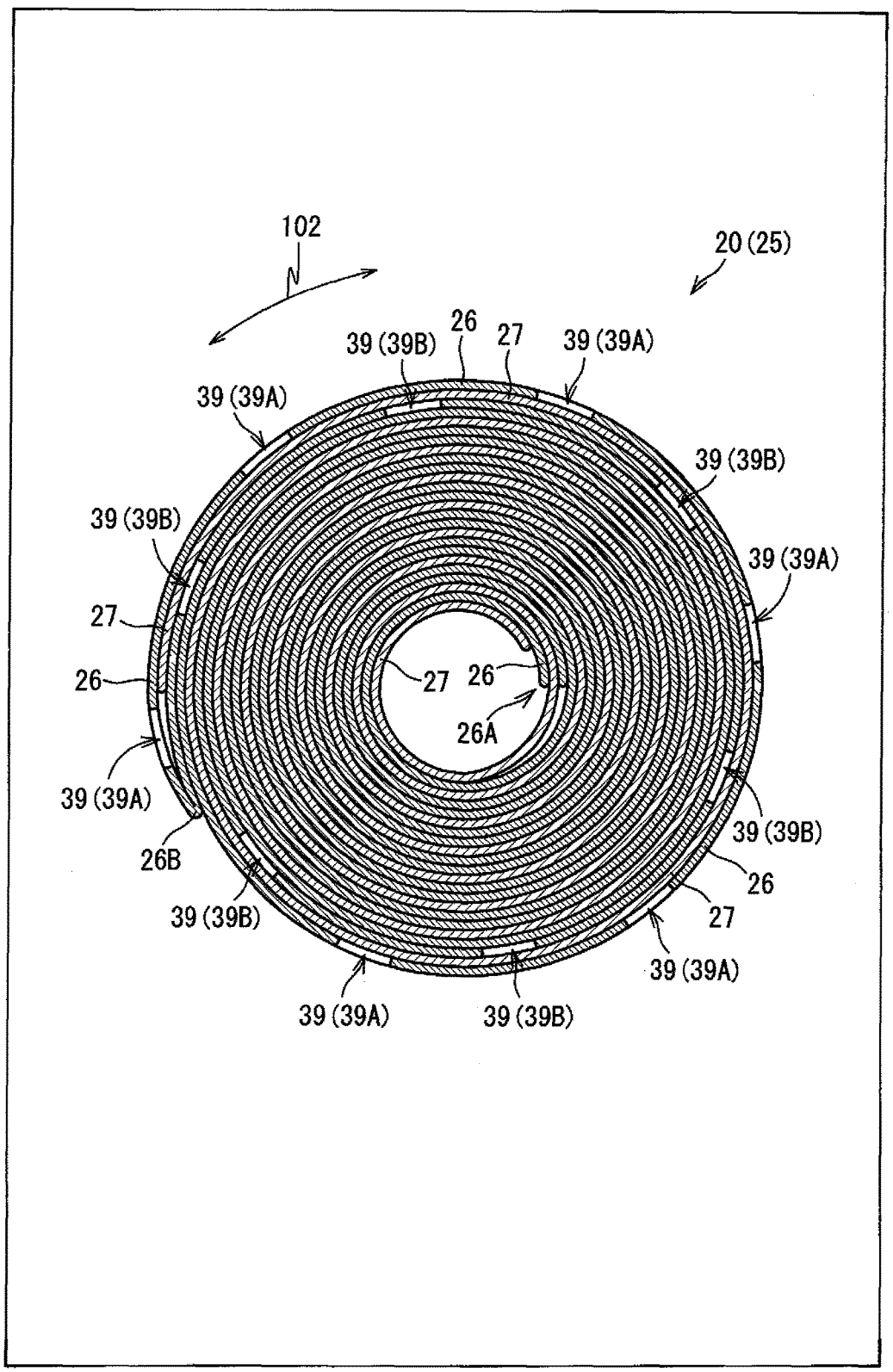
[FIG. 6]

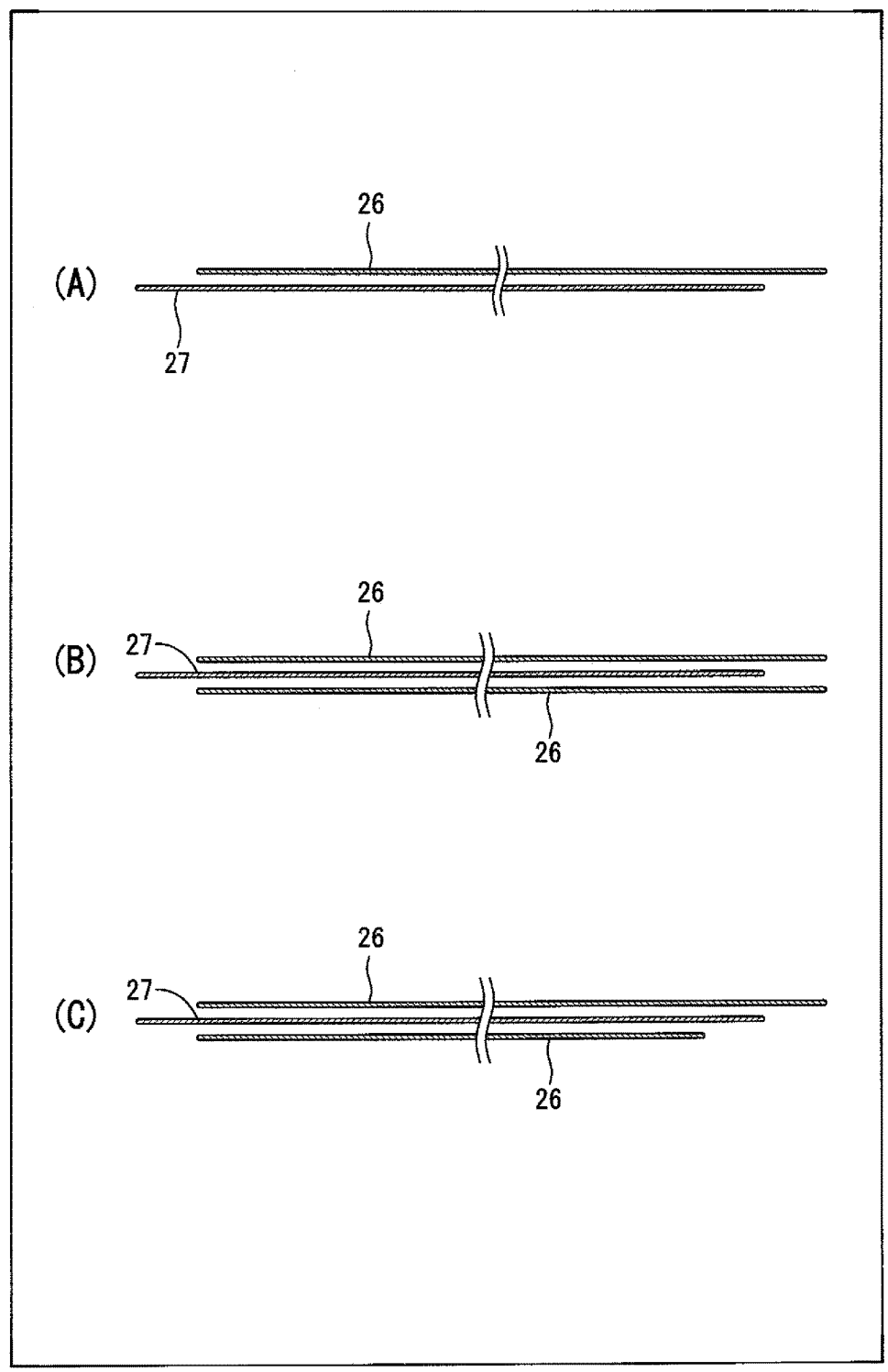

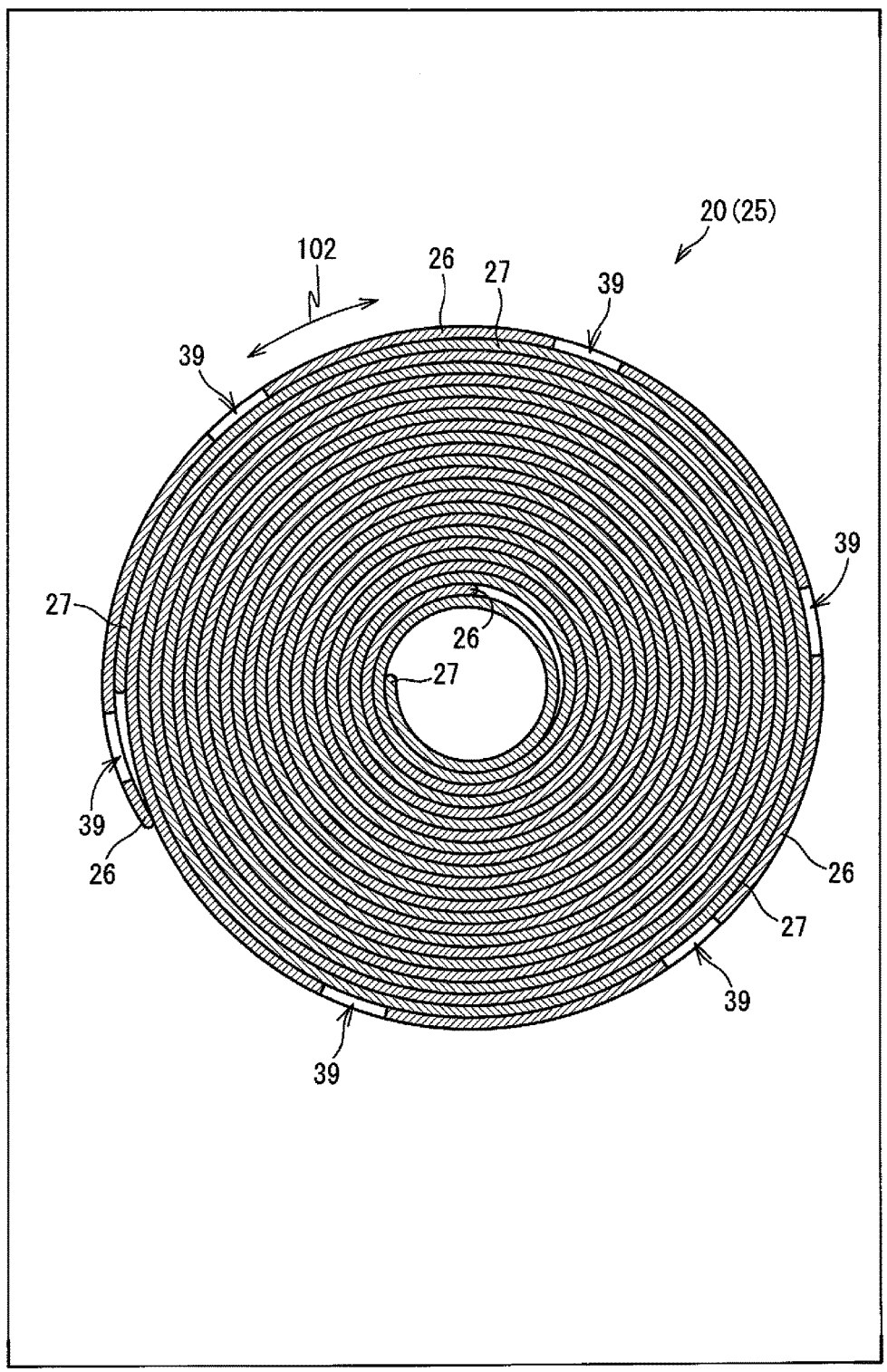
[FIG. 8]

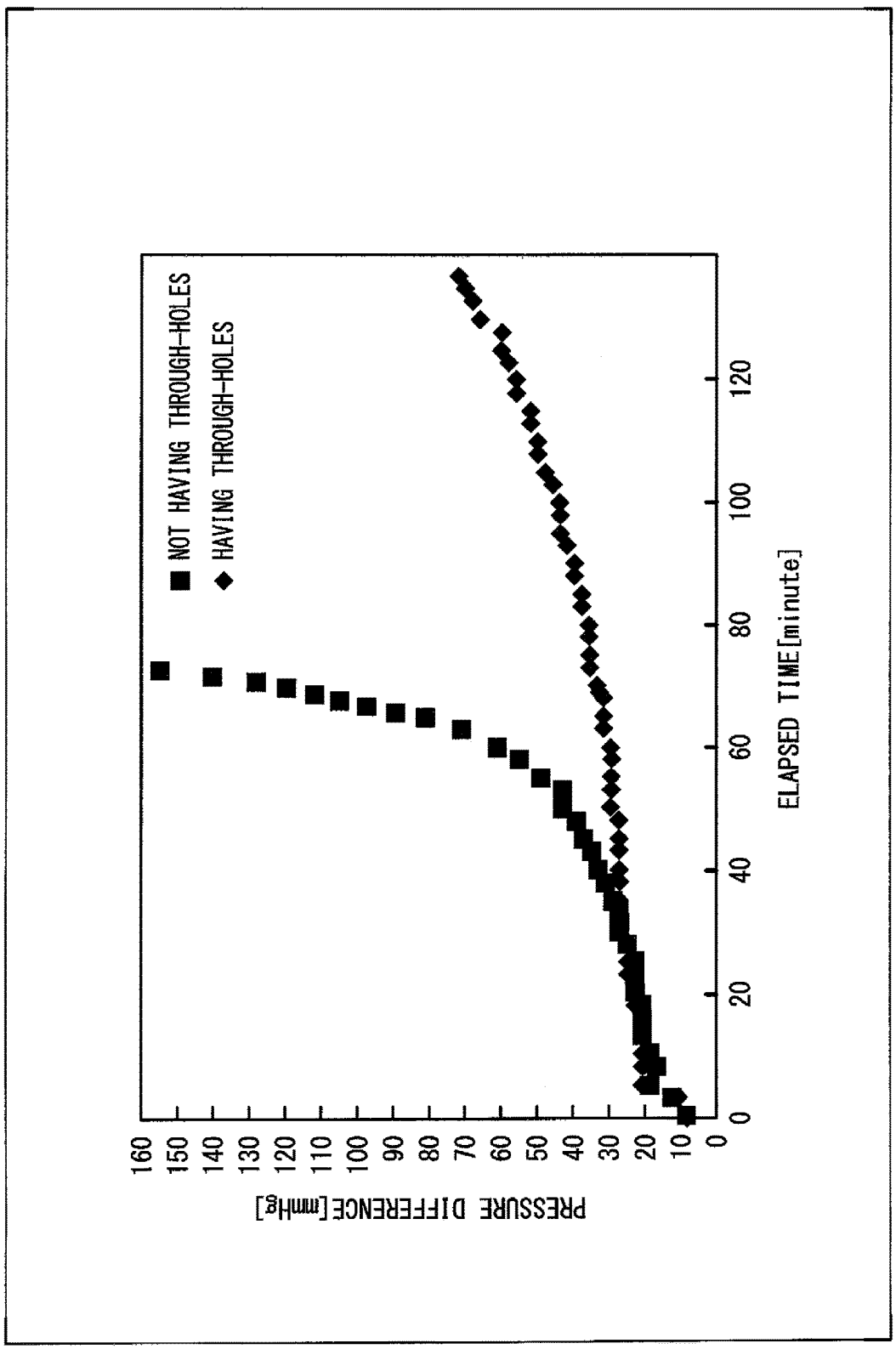
[FIG. 9]

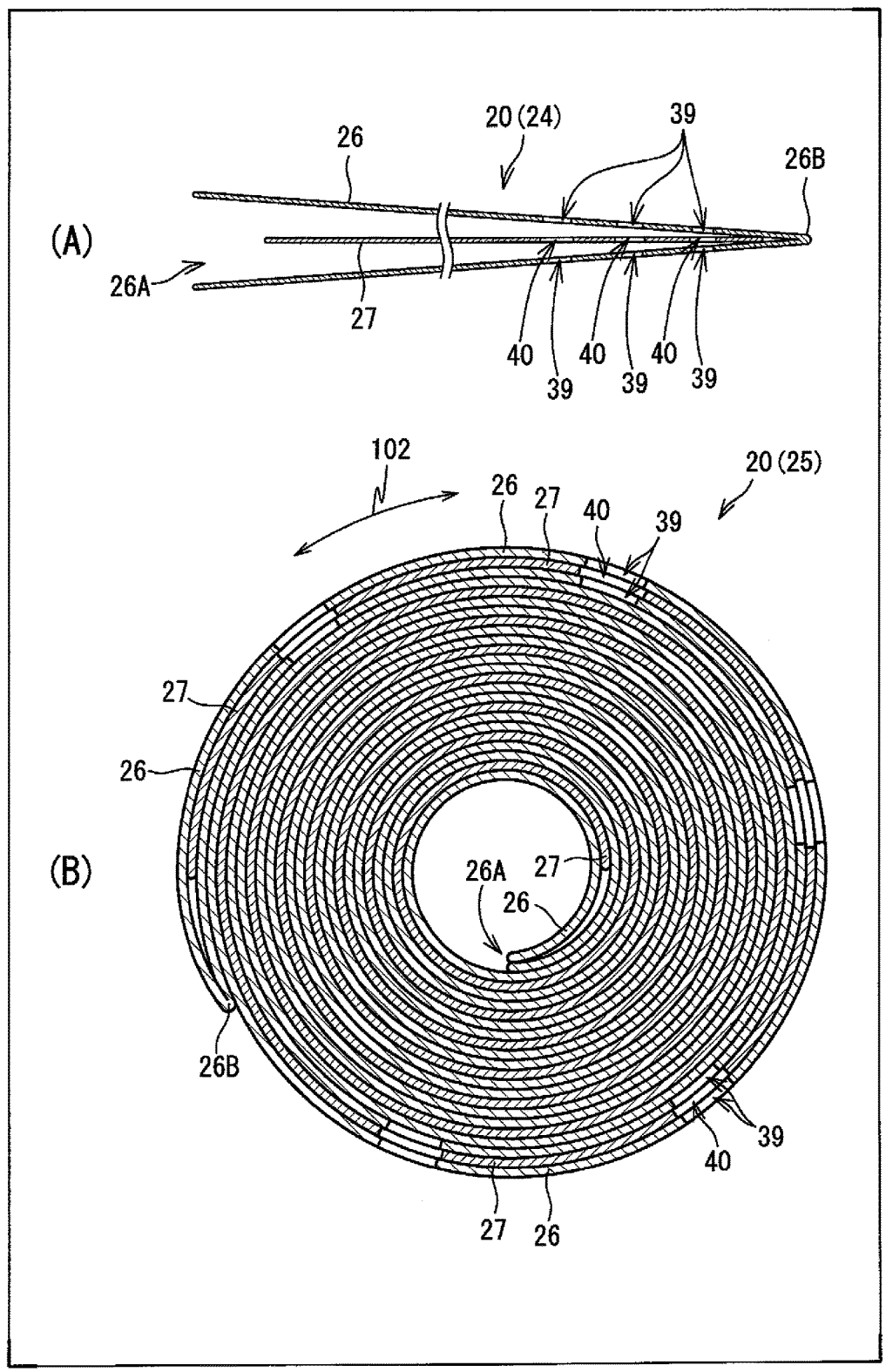
[FIG. 10]

[FIG. 11]
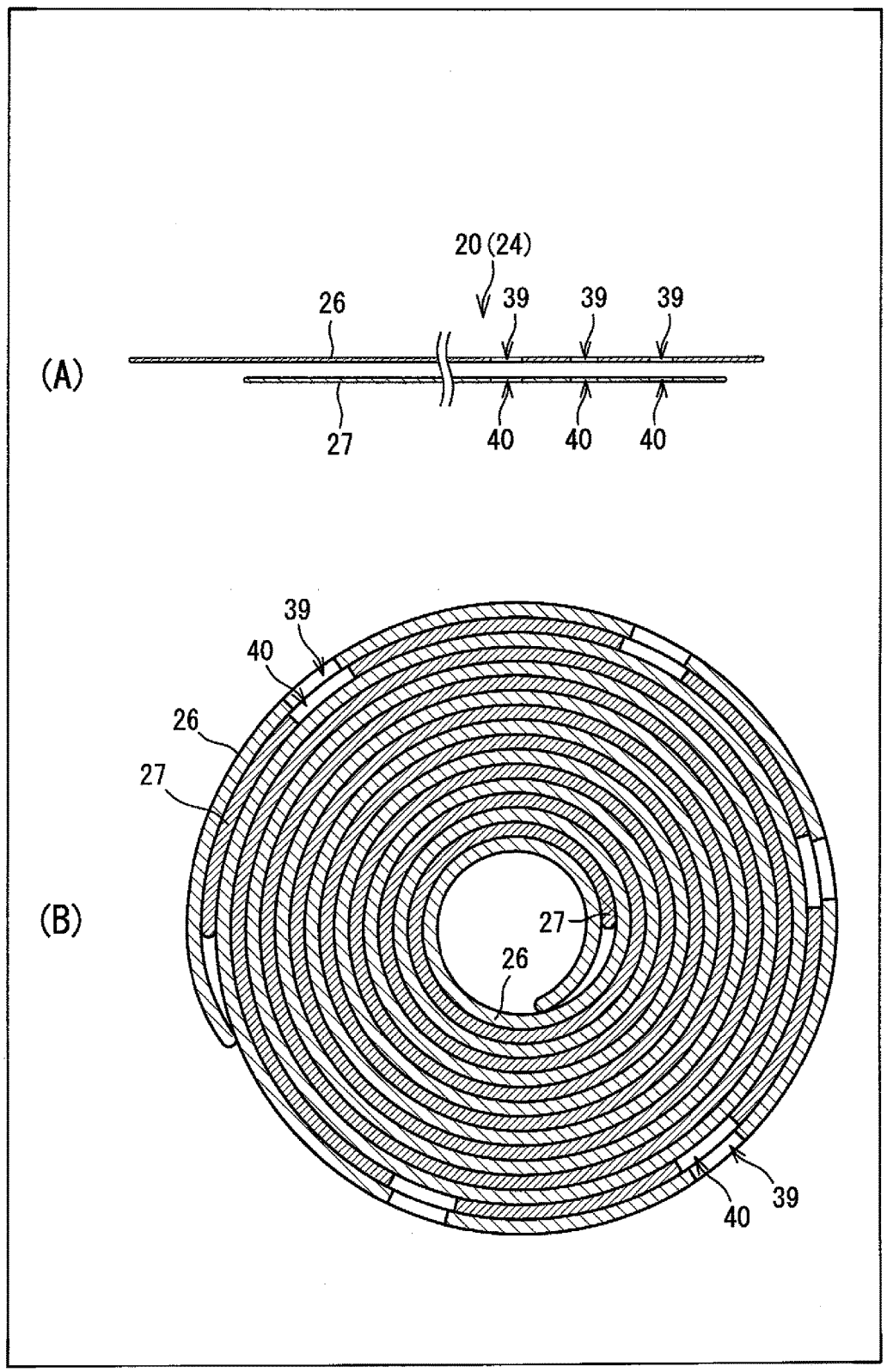

[FIG. 12]
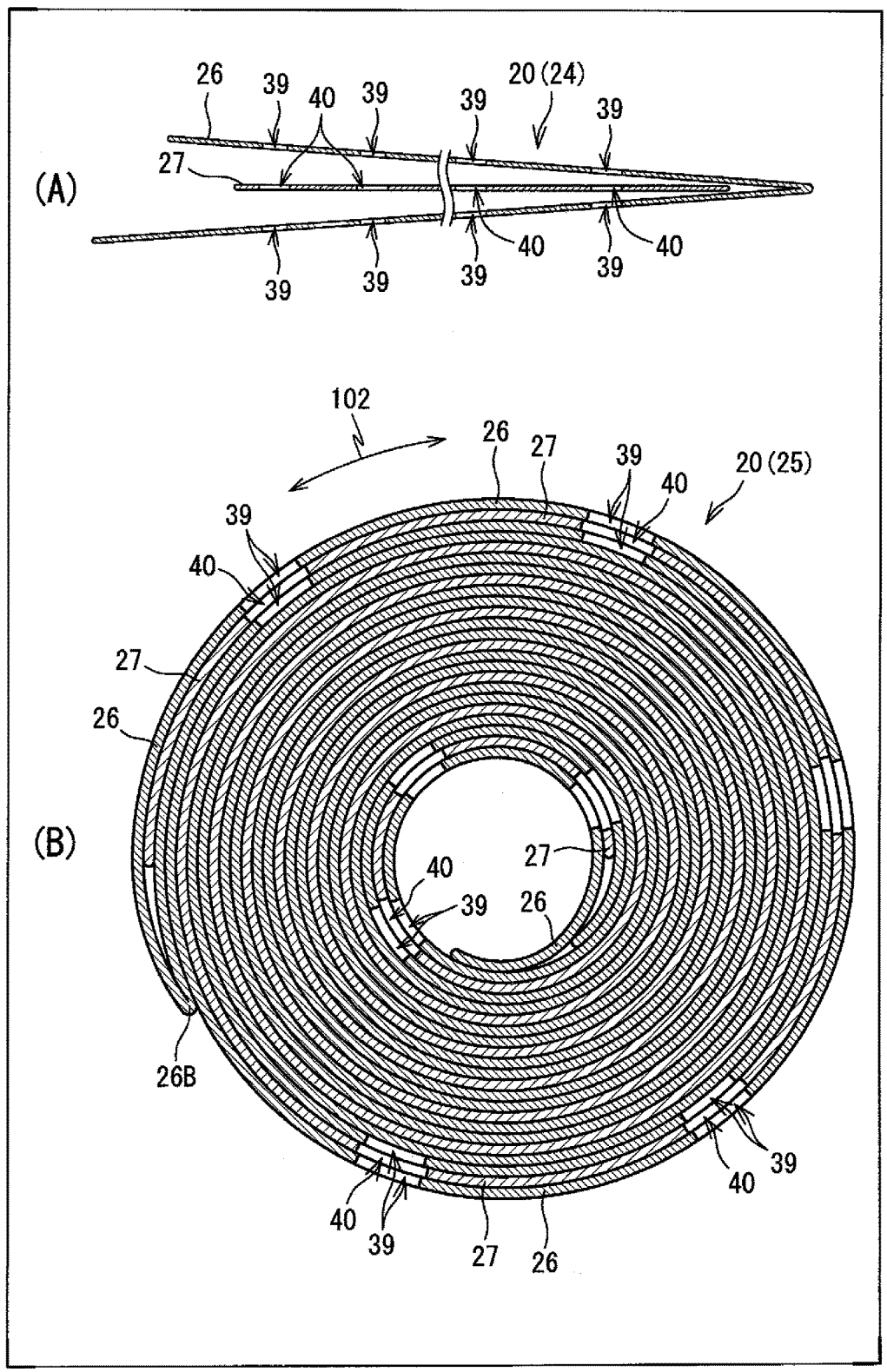

[FIG. 13]
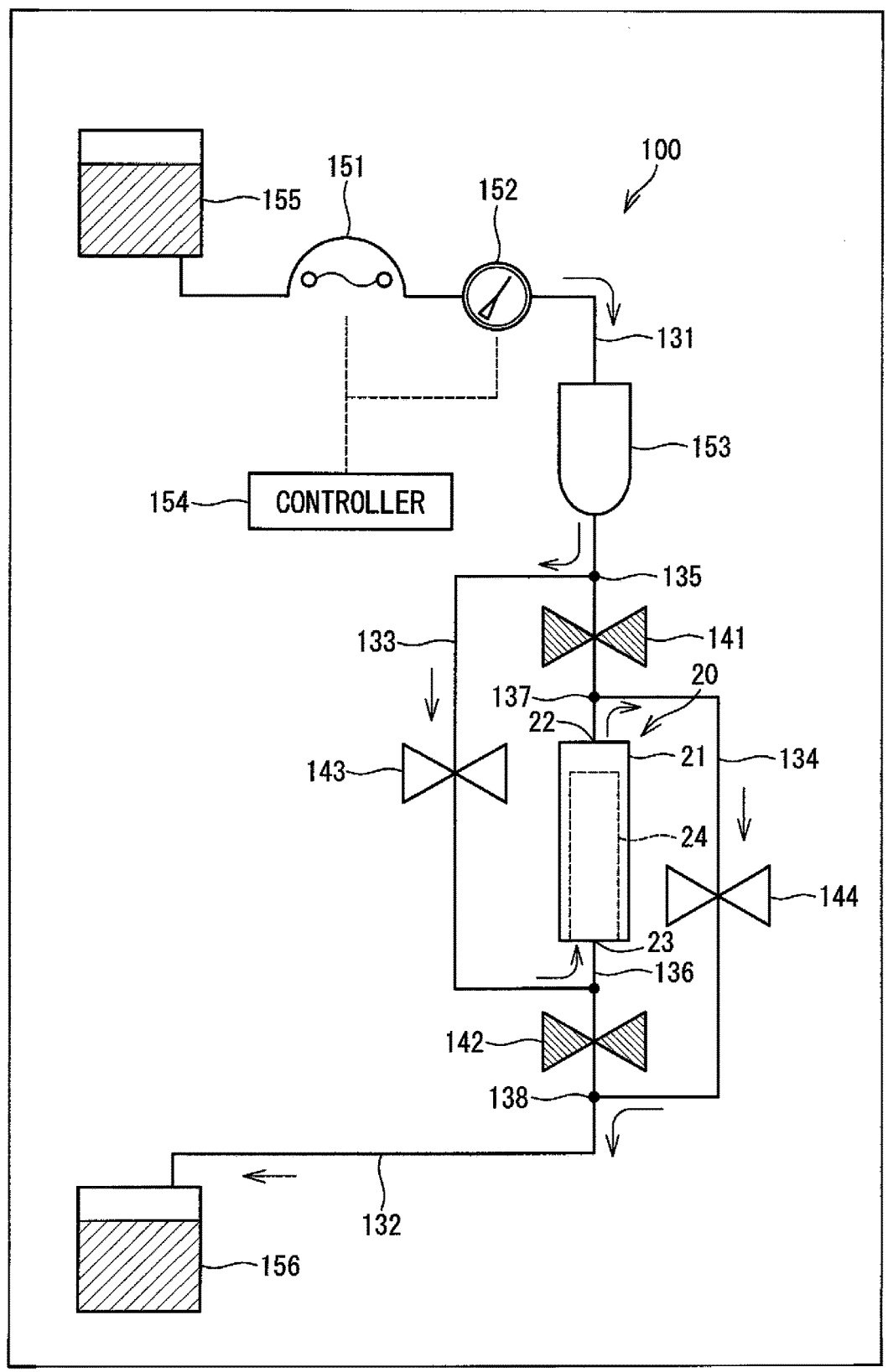

[FIG. 14]
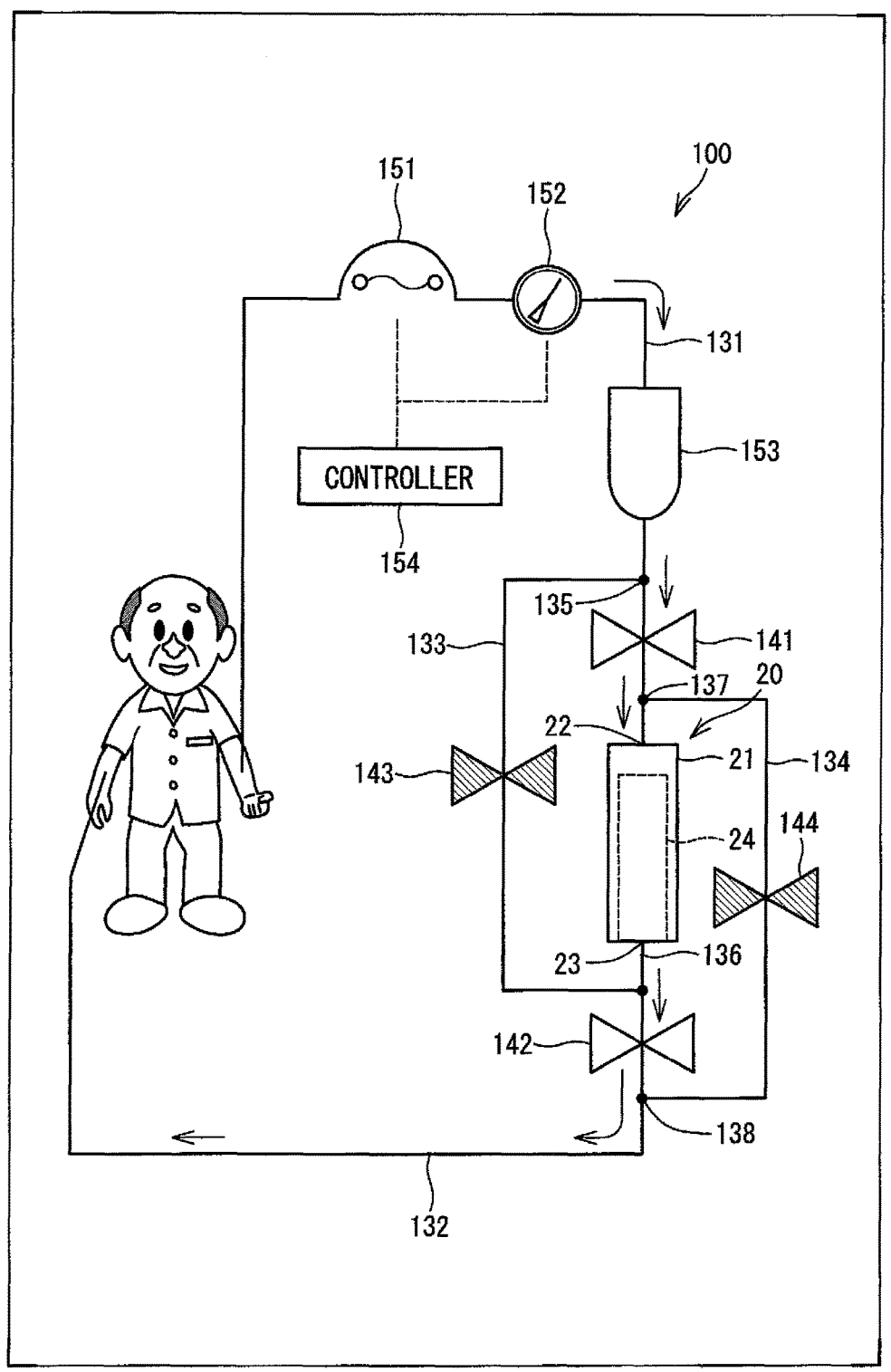

BLOOD TREATMENT FILTER DEVICE, PRIMING METHOD, AND BLOOD TREATMENT METHOD

CROSS-REFERENCE TO REALTED APPLICATIONS

This is the U.S. national phase of International Application No. PCT/JP2015/051337, filed Jan. 20, 2015, which claims the benefit of Japanese Patent Application Nos. 2014-009058, filed Jan. 22, 2014, and 2014-010214, filed Jan. 23, 2014, incorporated herein by reference in their entirety.

TECHNICAL FIELD

The present invention relates to a blood treatment filter device which removes specific components in blood, a priming method for the blood treatment filter device, and a blood treatment method using the blood treatment filter device.

BACKGROUND ART

Heretofore, a blood treatment filter device is known which removes specific components (typically leukocytes) in blood. The blood treatment filter device is a device which filters blood through a filter filled with nonwoven fabric and the like to remove specific components in the blood. Since the operation of the blood treatment filter device of the configuration described above is simple and the removal ratio of specific components in blood is high, the blood treatment filter device has been widely used heretofore.

Most of such blood treatment filter devices are configured by a wound body in which a filter sheet is cylindrically wound and in which specific components in blood are captured by the filter in a process in which the blood flows from the outer peripheral surface to the inner peripheral surface of the wound body. Such a blood treatment filter device has had a problem that, when the filter sheet is clogged on the outer peripheral surface side of the wound body, the blood becomes difficult to flow to the inside of the clogged portion, so that the pressure required for flowing the blood through the wound body becomes high.

To address such a problem, a configuration has been devised in which, in a blood treatment filter device having a cylindrical-shaped filter material in which a blood treatment filter layer and a spacer layer, through which blood more easily flows as compared with the blood treatment filter layer, are wound in a laminated state, an end portion of the spacer layer is exposed to the outer peripheral surface of the cylindrical-shaped filter material. According to this configuration, even when the blood treatment filter layer on the outermost periphery of the cylindrical-shaped filter material is clogged, blood flows into the inner peripheral surface side in a spiral shape along the spacer layer from the end portion of the spacer layer exposed to the outer peripheral surface, whereby the blood can reach the blood treatment filter layer on the inner peripheral surface side, so that specific components of the blood can be captured in the filter layer on the inner peripheral surface side (Patent Literature 1).

The blood treatment filter device needs to be subjected to priming treatment of introducing a priming liquid (for example, physiological saline) to remove foreign substance and air (hereinafter referred to as "air and the like") in a circuit before use. For example, Patent Literature 2 describes an example of priming treatment including a first process of charging a priming liquid into a retransfusion-side circuit from the outside and, simultaneously therewith, discharging an initial charged-liquid from the retransfusion-side circuit of a blood treatment unit and a second process of introducing the priming liquid to the blood treatment unit through the retransfusion-side circuit.

CITATION LIST

Patent Literature

Patent Literature 1: Japanese Patent No. 5164241
Patent Literature 2: Japanese Unexamined Patent Application Publication No. 2010-125208

SUMMARY OF INVENTION

Technical Problems

However, according to the blood treatment filter device described in Patent Literature 1, when the blood treatment filter layer on the outermost periphery is clogged, an entry port through which blood flows to the inner peripheral surface side relative to the spacer layer serves as space between the clogged blood treatment filter layer and the blood treatment filter layer located on the inner side with the spacer layer interposed between the filter layers. The blood flowing into the inner peripheral surface side of the clogged blood treatment filter device along the spacer layer from the entry port enters the blood treatment filter layer on the inner peripheral surface side which is not clogged in the vicinity of the entry port. Then, in the blood treatment filter layer on the inner peripheral surface side in the vicinity of the entry port, clogging is likely to occur. Due to the fact a chain of such clogging occurs, the entry port through which blood flows to the inner peripheral surface side of the clogged blood treatment filter layer extends in a long and narrow shape in the spiral direction, so that the pressure for flowing a large amount of blood to the long and narrow entry port may gradually become high. Moreover, the blood preferentially enters the blood treatment filter layer in the vicinity of the entry port, so that the use efficiency of the other blood treatment filter layers may become low.

Moreover, the priming treatment described in Patent Literature 2 has necessity of appropriately controlling the fluid flowing capability of a pump, the flow amount of the priming liquid flowing through each circuit and the initial charged-liquid, the timing at which the process proceeds to the second process from the first process, and the like. More specifically, the priming treatment described in Patent Literature 2 requires complicated operation of users, and thus, when the priming treatment is performed by unskilled workers, air and the like in the circuit may not be able to be completely removed.

The present invention has been made in view of the circumstances. It is an object of the present invention to provide a blood treatment filter device capable of efficiently utilizing a blood treatment filter layer.

It is another object of the present invention to provide a blood treatment filter device capable of performing priming easily and certainly, a priming method for the blood treatment filter device, and a blood treatment method employing the blood treatment filter device.

Solution to Problems (1) A blood treatment filter device according to the present invention has a filter sheet through which a specific component among components forming blood is harder to pass than other components and in which a filter through-hole is formed in the thickness direction, a spacer sheet through which the specific component is easier to pass than through the filter sheet, a wound body in which the filter sheet and the spacer sheet are laminated in the radial direction and are wound in a spiral shape in such a manner that the filter through-hole is located at least on the outer peripheral surface, seals of sealing both ends in the axial direction of the wound body in a fluid-tight manner, and a container having an internal space accommodating the wound body and having a blood inflow port connected in such a manner that blood can flow between the blood inflow port and the outer peripheral surface side of the wound body in the internal space and a blood outlet port connected in such a manner that blood can flow between the blood outlet port and the inner peripheral surface side of the wound body in the internal space.

According to the configuration described above, the blood flowing to the inner peripheral surface side from the outer peripheral surface side of the wound body can enter the filter sheet on the inner peripheral surface side through the filter through-hole formed in the filter sheet. Thus, the use efficiency of the filter sheet can be increased.

Moreover, by forming the filter through-hole in a wide range of the outer peripheral surface of the wound body, the number of entry routes through which the blood enters the filter sheet on the inner peripheral surface side can be increased.

Moreover, when filtration is performed, the blood can enter not only the filter sheet on the outer peripheral surface side but the filter sheet on the inner peripheral surface side through the filter through-hole, and therefore the volume of the filter sheet which the blood can enter can be increased. Thus, the size of the blood treatment filter device can be reduced in the axial direction of the wound body while maintaining the filtration capability equal to the filtration capability of former blood treatment filter devices in which no through-holes are formed.

(2) The spacer sheet has a spacer through-hole superimposed on the filter through-hole.

According to the configuration described above, when the inner peripheral surface side is viewed through the filter through-hole formed in the filter sheet of the outer peripheral surface, the filter sheet on the inner peripheral surface side is exposed through the filter through-hole and the spacer through-hole superimposed on the filter through-hole. Therefore, the blood can flow into the filter sheet on the inner peripheral surface side through the filter through-hole and the spacer through-hole which are formed in the wound body without passing through the spacer sheet.

(3) The spacer through-hole on the inner peripheral side by one turn relative to the filter through-hole located on the outer peripheral surface is larger than the filter through-hole located on the outer peripheral surface.

According to the configuration described above, the spacer through-hole on the inner peripheral side by one turn relative to the through-hole located on the outer peripheral surface is larger than the filter through-hole located on the outer peripheral surface. Therefore, due to the fact that the filter sheet and the spacer sheet are wound, even in the case where the positions in the circumferential direction of the filter through-hole and the spacer through-hole are deviated from each other, a possibility that the superposition in the circumferential direction of both the through-holes can be maintained can be made high.

(4) The filter through-hole is not superimposed on other filter through-holes disposed on the outer peripheral side and the inner peripheral side by one turn of the wound body relative to the through-hole in the wound body.

According to the configuration described above, when the blood flows from the outer peripheral surface side to the inner peripheral surface side of the wound body along the radial direction of the wound body, for example, the blood flowing into the filter sheet on the inner peripheral surface side by one turn through the filter through-hole formed in the filter sheet of a certain peripheral surface reaches a region which is not the filter through-hole of the filter sheet to enter the filter sheet. More specifically, by not overlapping the filter through-holes as in the configuration above, the surface area of the filter sheet which the blood can enter can be enlarged. Thus, the use efficiency of the filter sheet can be increased.

(5) The wound body has a laminated sheet spirally wound in a state where an end portion of the side opposite to a fold of the filter sheet is located on the inner peripheral surface side, and the laminated sheet is configured so that the spacer sheet is sandwiched between the filter sheet folded in half.

According to the configuration described above, since the filter sheet is disposed on both the back-and-front surface sides of the spacer sheet, the proportion of the filter sheet in the wound body can be increased. Moreover, since the spacer sheet is made to abut on the filter sheet on both sides, the deviation of the spacer sheet to the filter sheet can be reduced.

(6) At least one part of the inner peripheral surface of the wound body is formed by the spacer sheet.

According to the configuration described above, even when a situation that the filter sheet is clogged, so that the blood cannot enter the filter sheet occurs, the blood can reach the inner peripheral surface of the wound body through the spacer sheet from the filter through-hole formed in the filter sheet on the outer peripheral surface. Thus, the occurrence of the situation that the blood cannot pass through the wound body can be prevented.

(7) The inner peripheral surface of the wound body is formed by the filter sheet. The wound body is a spirally wound one in such a manner that the filter through-hole is also located on the inner peripheral surface. The spacer through-hole located on the outer peripheral side by one turn relative to the inner peripheral surface is larger than the filter through-hole located on the inner peripheral surface.

According to the configuration described above, even in the case where a portion forming the inner peripheral surface of the wound body in the filter sheet is clogged, the blood can pass through the inner peripheral surface through the filter through-hole and the spacer through-hole which are formed in the portion.

Moreover, according to the configuration described above, the spacer through-hole on the outer peripheral side by one turn relative to the filter through-hole located on the inner peripheral surface is larger than the filter through-hole located on the inner peripheral surface. Therefore, due to the fact that the filter sheet and the spacer sheet are wound, even in the case where the positions in the circumferential direction of the filter through-hole and the spacer through-hole are deviated from each other, a possibility that the superposition in the circumferential direction of both the through-holes can be maintained can be made high as in the case of (3) above.

(8) A priming method according to the present invention is performed to a blood treatment filter device having a body container which has a first port and a second port which are continuous to the internal space and which is disposed with the first port located above the second port in the gravity direction, a blood treatment filter in a dry state placed in the internal space of the body container, a first blood circuit which is connected to the first port and through which liquid flows, a second blood circuit which is connected to the second port and through which liquid flows, a first bypass circuit which is connected to the first blood circuit and the second blood circuit and through which liquid flows, and a second bypass circuit which is connected to the side closer to the first port relative to the connection position of the first bypass circuit in the first blood circuit and is connected to the side further from the second port relative to the connection position of the first bypass circuit in the second blood circuit and through which liquid flows. The priming method includes individually closing the circuit between the connection position of the first bypass circuit and the connection position of the second bypass circuit in each of the first blood circuit and the second blood circuit to cause a priming liquid to flow into the internal space of the body container from the first blood circuit through the first bypass circuit, the second blood circuit, and the second port, and then to cause the priming liquid to flow out of the internal space of the body container to the second blood circuit through the first port, the first blood circuit, and the second bypass circuit.

According to the configuration described above, the priming treatment can be performed only by supplying the priming liquid through the first blood circuit in the state where the first blood circuit and the second blood circuit are closed in the circuits between the connection positions of the first bypass circuit and the second bypass circuit. Moreover, since the priming liquid is caused to flow into the body container through the second port located below in the gravity direction, and then the priming liquid is caused to flow out of the body container through the first port located above in the gravity direction, air and the like in the body container can be certainly pressed out. More specifically, priming can be performed easily and certainly.

(9) The blood treatment filter has a sheet shape and is placed in the body container in a cylindrically wound state. The body container has a liquid flow passage which causes the first port and the internal space on the outer peripheral surface side of the cylindrical-shaped blood treatment filter to be continuous to each other and a liquid flow passage which causes the internal space on the inner peripheral surface side of the cylindrical-shaped blood treatment filter and the second port to be continuous to each other.

According to the configuration described above, the priming liquid flowing into the body container through the second port passes through the blood treatment filter outwardly in the radial direction through the flow passage on the inner peripheral surface side, and then flows out of the first port through the flow passage on the outer peripheral surface side. On the other hand, the blood flowing into the body container through the first port described later passes through the blood treatment filter inwardly in the radial direction through the flow passage on the outer peripheral surface side, and then flows out of the second port through the flow passage on the inner peripheral surface side.

(10) A blood treatment method according to the present invention includes, in the blood treatment filter device subjected to the priming method described above, closing the first bypass circuit and the second bypass circuit, and then individually opening the circuit between the connection position of the first bypass circuit and the connection position of the second bypass circuit in each of the first blood circuit and the second blood circuit to cause the blood to flow into the body container through the first port from the first blood circuit, and then to cause the blood to flow out to the second blood circuit through the second port from the body container.

According to the configuration described above, blood filter treatment can be performed using the blood treatment filter device only by opening the first blood circuit and the second blood circuit which are closed in the priming treatment and opening the first bypass circuit and the second bypass circuit.

(11) A blood treatment filter device according to the present invention has a body container which has a first port and a second port which are continuous to the internal space and which is disposed with the first port located above the second port in the gravity direction, a blood treatment filter in a dry state placed in the internal space of the body container, a first blood circuit which is connected to the first port and through which liquid flows, a second blood circuit which is connected to the second port and through which liquid flows, a first bypass circuit which is connected to the first blood circuit and the second blood circuit and through which liquid flows, a second bypass circuit which is connected to the side closer to the first port relative to the connection position of the first bypass circuit in the first blood circuit and is connected to the side further from the second port relative to the connection position of the first bypass circuit in the second blood circuit and through which liquid flows, a valve which opens/closes the circuit between the connection position of the first bypass circuit and the connection position of the second bypass circuit in the first blood circuit, a valve which opens/closes the circuit between the connection position of the first bypass circuit and the connection position of the second bypass circuit in the second blood circuit, a valve which opens/closes the first bypass circuit, and a valve which opens/closes the second bypass circuit.

(12) The blood treatment filter has a sheet shape and placed in the body container in a cylindrically wound state. The body container has a liquid flow passage which causes the first port and the internal space on the outer peripheral surface side of the cylindrical-shaped blood treatment filter to be continuous to each other and a liquid flow passage which causes the internal space on the inner peripheral surface side of the cylindrical-shaped blood treatment filter and the second port to be continuous to each other.

Advantageous Effects of Invention

According to the present invention, the blood which flows from the outer peripheral surface side into the inner peripheral surface side of the wound body can enter the filter sheet on the inner peripheral surface side through the filter through-hole formed in the filter sheet, and therefore the filter sheet can be efficiently utilized.

Moreover, according to the present invention, the priming treatment can be performed only by supplying the priming liquid through the first blood circuit in the state where the first blood circuit and the second blood circuit are closed between the connection positions of the first bypass circuit and the second bypass circuit. Moreover, since the priming liquid is caused to flow into the body container through the second port located below in the gravity direction, and then the priming liquid is caused to flow out of the body container through the first port located above in the gravity direction, air and the like in the body container can be certainly pressed out. More specifically, the priming can be performed easily and certainly.

BRIEF DESCRIPTION OF DRAWINGS

FIG. 1 is a cross sectional view of a filter device 20 in this embodiment.

FIG. 2 are views illustrating a blood cell removal filter 24 in this embodiment, in which FIG. 2A is a schematic cross sectional view of the blood cell removal filter 24 and FIG. 2B is a view illustrating the structure in a state where a wound body 25 forming the blood cell removal filter 24 is in a non-winding state.

FIG. 3 is a front view of the wound body 25.

FIG. 4 is a cross sectional view of the wound body 25.

FIG. 5 are front views of a wound body 25 in modification 2.

FIG. 6 is a cross sectional view of the wound body 25 in the modification 2.

FIG. 7 are views illustrating the structure in a state where the wound body 25 is in a non-winding state in modification 4.

FIG. 8 is a cross sectional view of the wound body 25 in the modification 4.

FIG. 9 is a graph showing the pressure differences to the elapsed time of Example and Comparative Example.

FIG. 10(A) is a view illustrating the structure in a state where the wound body 25 is in a non-winding state in the modifications 3 and 5 and FIG. 10(B) is a cross sectional view of the wound body 25 in the modifications 3 and 5.

FIG. 11(A) is a view illustrating the structure in a state where the wound body 25 is in a non-winding state in the modifications 4 and 5 and FIG. 11(B) is a cross sectional view of the wound body 25 in the modifications 4 and 5.

FIG. 12 are cross sectional views of the wound body 25 in modification 6.

FIG. 13 is a schematic view of a blood treatment filter device 100 in the embodiments and illustrates the state of valves 141 to 144 when priming treatment is performed.

FIG. 14 is a schematic view of the blood treatment filter device 100 in the embodiments and illustrates the state of the valves 141 to 144 when blood filter treatment is performed.

DESCRIPTION OF EMBODIMENTS

Hereinafter, embodiments of the present invention are described with reference to the drawings. It is a matter of course that the embodiments describe only one example of the present invention and the embodiments may be altered as appropriate insofar as the scope of the present invention is not altered.

[First Embodiment]

A filter device 20 (an example of the blood treatment filter device of the present invention) in this embodiment is configured by a cylindrical-shaped body container 21 (an example of the container of the present invention) having internal space and a blood cell removal filter 24 which is placed in the internal space of the body container 21 as illustrated in FIG. 1. The filter device 20 is a device which performs blood cell removal treatment of removing blood cells (typically leukocytes but other components may be acceptable) from supplied blood, i.e., filtering blood, and then discharging the filtered blood. The details of the blood cell removal treatment are described later. The blood is usually human blood but blood of animals other than human beings may be acceptable.

The body container 21 is formed with a thermoplastic resin, such as polycarbonate, for example. As illustrated in FIG. 1, the body container 21 has a first port 22 (an example of the blood inflow port of the present invention) and a second port 23 (an example of the blood outlet port of the present invention) which are continuous to the internal space. The first port 22 is provided on the end surface of one side of the body container 21 and is connected to a first blood circuit 131 (refer to FIG. 14). Herein, the first blood circuit 131 is a circuit in which one end is connected to a patient and the other end is connected to the first port 22 and which flows blood from the patient to the first port 22. The first blood circuit 131 is provided with a pump 151, a pressure sensor 152, and a chamber 153.

The second port 23 is provided on the end surface of the other side of the body container 21 and is connected to a second blood circuit 132 (refer to FIG. 14). Herein, the second blood circuit 132 is a circuit in which one end is connected to the second port 23 and the other end is connected to a patient and which flows blood from the second port 23 to the patient. The second blood circuit 132 may be provided with a pressure sensor and a chamber. It is a matter of course that, in the first embodiment, the first blood circuit 131 and the second blood circuit 132 are only examples and the configurations of these blood circuits may be altered as appropriate.

The body container 21 during the use of the blood cell removal device 10 is disposed in a state where the first port 22 is located above the second port 23 in the gravity direction.

The blood cell removal filter 24 is configured by a cylindrical-shaped wound body 25 in which a filter sheet 26 and a spacer sheet 27 (refer to FIG. 2(B)) are spirally wound in an overlapped state as illustrated in FIG. 2(A), a cylindrical-shaped exterior sheet 28 covering the outer peripheral surface of the wound body 25, and seals 31 provided at both end portions in the longitudinal direction of the wound body 25. More specifically, the blood cell removal filter 24 presents a cylindrical shape as a whole. The wound body 25 is a long sheet formed by overlapping the filter sheet 26 and the spacer sheet 27 as illustrated in FIG. 2(B).

The filter sheet 26 is formed with a porous material which adsorbs specific components among the components forming blood and, for example, nonwoven fabric containing polyester, polypropylene, polyethylene terephthalate, polytetrafluoroethylene, and the like is mentioned. These materials may be subjected to various kinds of surface treatment for controlling the blood cell component permeability for use. For example, these materials may be subjected to hydrophilization treatment for use. The average pore size of the filter sheet 26 containing the porous material is preferably set to be large in such a manner as not to impair the blood fluidity and not to increase the pressure loss of the filter and to be small in such a manner as to be able to secure a moderate leukocyte removal ratio.

As described above, the specific components (leukocytes in this embodiment) are harder to pass through the filter sheet 26 than the other components (for example, erythrocytes) among the components contained in the blood. Although the cells to be removed from blood are leukocytes in this embodiment, the cells to be removed from blood may be cells other than the leukocytes.

The spacer sheet 27 is a net-like sheet. The average pore size of the spacer sheet 27 is set to be larger than the average pore size of the filter sheet 26. Thus, the specific components described above are easier to pass through the spacer sheet 27 than through the filter sheet 26.

The wound body 25 is formed as illustrated in FIG. 3 and FIG. 4 by spirally winding one in which the spacer sheet 27 is sandwiched between the filter sheet 26 folded in half illustrated in FIG. 2(B). More specifically, the wound body 25 is formed by spirally winding the filter sheet 26 and the spacer sheet 27 in an overlapped state.

As illustrated in FIG. 2(B), the spacer sheet 27 is partially exposed from an open side end portion 26A of the filter sheet 26 in the state where the spacer sheet 27 is sandwiched between the filter sheets 26. For example, the length in the longitudinal direction of the filter sheet 26 is about 1600 mm and the length in the longitudinal direction of the spacer sheet 27 is about 850 mm. The spacer sheet 27 is disposed in a state where the spacer sheet 27 is 20 mm deviated to the open side of the filter sheet 26. Thus, the length of the spacer sheet 27 exposed from the open side end portion 26A of the filter sheet 26 is about 70 mm. It is a matter of course that the spacer sheet 27 may not be deviated to the open side of the filter sheet 26. In this case, the length of the spacer sheet 27 exposed from the open side end portion 26A of the filter sheet 26 is about 50 mm. The wound body 25 is formed into a cylindrical shape illustrated in FIG. 2(A), FIG. 3, and FIG. 4 by spirally winding the filter sheet 26 with the open side end portion 26A of the filter sheet 26, i.e., an end portion on the side opposite to the fold of the filter sheet 26 located on the inside and with a fold side end portion 26B located on the outside.

In FIG. 2(A), since the wound body 25 is illustrated in a simplified manner, the filter sheet 26 and the spacer sheet 27 are not distinguished but the filter sheet 26 and the spacer sheet 27 are distinguished in FIG. 4.

As illustrated in FIG. 4, the spacer sheet 27 exposed from an open side end portion 26A of the filter sheet 26 forms the entire inner peripheral surface of the wound body 25. More specifically, the inner peripheral surface of the wound body 25 is formed only by the spacer sheet 27.

The spacer sheet 27 exposed from the open side end portion 26A of the filter sheet 26 does not always need to form the entire inner peripheral surface of the wound body 25. For example, the spacer sheet 27 may form a part of the inner peripheral surface of the wound body 25 by being slightly exposed from the open side end portion 26A of the filter sheet 26. More specifically, the inner peripheral surface of the wound body 25 may be formed by the spacer sheet 27 and the filter sheet 26.

As illustrated in FIG. 2(B), the spacer sheet 27 is sandwiched between the filter sheets 26 in a portion other than the open side end portion 26A (end portion located on the inner peripheral surface side in the wound state). Thus, the outer peripheral surface of the wound body 25 is formed by the filter sheet 26 as illustrated in FIG. 4.

As illustrated in FIG. 2(B), FIG. 3, and FIG. 4, a plurality of filter through-holes 39 are formed in the filter sheet 26. The plurality of filter through-holes 39 are disposed at equal intervals along the axial direction 101 of the wound body 25 as illustrated in FIG. 3. Moreover, the plurality of filter through-holes 39 are disposed at equal intervals along the circumferential direction 102 of the wound body 25 as illustrated in FIG. 3 and FIG. 4. The number of the filter through-holes 39 may be only one.

The filter through-holes 39 are formed in a circular shape. The diameter of the filter through-holes 39 is set to a length in such a manner as not to block the blood flow. The diameter of the filter through-holes 39 is preferably 1 mm to 10 mm and more preferably 3 mm to 7 mm. In this embodiment, the diameter of the filter through-holes 39 is 5 mm.

Although the intervals in the axial direction 101 of the plurality of filter through-holes 39 have the same length and the intervals in the circumferential direction 102 of the plurality of filter through-holes 39 have the same length in this embodiment, the length of each interval may vary. In this embodiment, although the filter through-holes 39 have a circular shape but may have a shape other than the circular shape. For example, the filter through-holes 39 may have an oval shape.

As illustrated in FIG. 2(B), the plurality of filter through-holes 39 are formed only on one side (upper side relative to the fold in FIG. 2(B)) with respect to the fold in the spacer sheet 27. Moreover, the plurality of filter through-holes 39 are formed only on the fold side (in detail, a range of a predetermined length from the fold to the open side end portion 26A side) in the spacer sheet 27. The plurality of filter through-holes 39 are formed only in the filter sheet 26 on the outer peripheral surface of the wound body 25 as illustrated in FIG. 4. More specifically, the range of the predetermined length is the range of the length along the circumferential direction 102 of the filter sheet 26 on the outer peripheral surface of the wound body 25. The filter through-holes 39 may be formed also in the filter sheet 26 other than the filter sheet 26 on the outer peripheral surface of the wound body 25.

The exterior sheet 28 illustrated in FIG. 2(A) is a net-like sheet formed with a material harder than a material of the wound body 25. The exterior sheet 28 is a tricot material obtained by knitting fibers, for example. The average pore size of the exterior sheet 28 is desirably set to be larger than the average pore size of the filter sheet 26. The exterior sheet 28 is formed into a cylindrical shape having an outer diameter size larger than the outer diameter size of the wound body 25 and holds the wound body 25 thereinside. By attaching the fold side end portion 26B of the filter sheet 26 to the inner peripheral surface of the exterior sheet 28, the shape of the wound body 25 is maintained.

As illustrated in FIG. 1, seals 31 hardened by an adhesive or the like are provided at both end portions in the longitudinal direction (axial direction 101 illustrated in FIG. 1) of the wound body 25. The seals 31 do not allow the passage of liquid by being hardened by an adhesive or the like. More specifically, the seals 31 seal both end portions in the longitudinal direction of the wound body 25 in a fluid-tight manner. The seals 31 are not limited to the configuration in which the seals 31 are hardened by an adhesive or the like insofar as both the end portions in the longitudinal direction of the wound body 25 can be sealed in a fluid-tight manner. For example, the seals 31 may be members formed with rubber or the like which do not allow the passage of liquid and the member may be attached to both the end portions in the longitudinal direction of the wound body 25.

A through-hole 33 is formed in the central portion of one of the seals 31 provided at both the end portions of the wound body 25. The through-hole 33 is continuous to the internal space of the blood cell removal filter 24 defined by the inner peripheral surface and the seals 31 of the wound body 25.

The blood cell removal filter 24 is attached to the wall surface (wall surface serving as the bottom surface during use) of the body container 21 in which the second port 23 is formed as illustrated in FIG. 1. The length in the axial direction 101 (height in FIG. 1) of the blood cell removal filter 24 is shorter than the length in the axial direction 101 of the internal space of the body container 21. The outer diameter size of the blood cell removal filter 24 is smaller than the internal diameter size (i.e., diameter of the internal space) of the body container 21. As a result, a gap is formed between the wall surface (wall surface serving as the top surface during use) of the body container 21 in which the first port 22 is formed and the blood cell removal filter 24 and a gap is formed between the inner peripheral surface of the body container 21 and the outer peripheral surface of the blood cell removal filter 24. The gaps serve as a flow passage 29 leading to the first port 22. More specifically, in the body container 21, the first port 22 and the internal space on the outer peripheral surface side of the blood cell removal filter 24 are continuous to each other by the flow passage 29.

The blood cell removal filter 24 is attached to the wall surface of the body container 21 by bonding the seal 31 in which the through-hole 33 is formed and the wall surface (wall surface serving as the bottom surface during use) of the body container 21. In this case, the blood cell removal filter 24 is attached to the wall surface of the body container 21 in such a manner that the through-hole 33 and the second port 23 provided in the wall surface of the body container 21 are superimposed on each other. Thus, the internal space of the blood cell removal filter 24 is continuous to the second port 23 through the through-hole 33. The internal space of the blood cell removal filter 24 serves as a flow passage 30 leading to the second port 23. More specifically, the internal space on the inner peripheral surface side of the blood cell removal filter 24 and the second port 23 are continuous to each other by the flow passage 30 in the body container 21.

The blood cell removal filter 24 is attached to the wall surface of the body container 21 in such a manner as to completely cover the through-hole 33. Thus, the joint between the through-hole 33 and the flow passage 29 is sealed in a fluid-tight manner by the seal 31 and the wall surface of the body container 21 bonded to each other.

As described above, in the state where the blood cell removal filter 24 is attached to the body container 21, the first port 22 is continuous to the internal space on the outer peripheral surface side of the blood cell removal filter 24. The second port 23 is continuous to the internal space on the inner peripheral surface side of the blood cell removal filter 24.

Next, blood cell removal treatment using the filter device 20 in this embodiment is described. First, the filter device 20 is connected to a first blood circuit 131 and a second blood circuit 132. Thus, the flow of blood from the first blood circuit 131 to the first port 22 is permitted and the flow of blood from the second port 23 to the second blood circuit 132 is permitted. Next, a pump 151 of the first blood circuit 131 is driven under the control by the controller 154 (refer to FIG. 14), whereby blood is caused to flow out of a patient into the first blood circuit 131.

The blood which flows into the internal space of the body container 21 through the first port 22 from the first blood circuit 131 does not flow into the seal 31. Therefore, as illustrated in FIG. 1, the blood flows to the outer peripheral surface side of the blood cell removal filter 24 along the flow passage 29 to pass through the blood cell removal filter 24 from the outer peripheral surface side to the inner peripheral surface side (i.e., inwardly in the radial direction). In this process, leukocytes contained in the blood are captured by the blood cell removal filter 24 (mainly filter sheet 26). More specifically, the blood is filtered. This process is described later in more detail.

The filtered blood flows out of the flow passage 30 into the second blood circuit 132 through the through-hole 33 and the second port 23, and then returned to the patient. In FIG. 1, the blood flow in the flow passages 29 and 30 is indicated by the arrow and the blood flow in the blood cell removal filter 24 is indicated by the white arrow.

Next, the process in which the blood passes through the blood cell removal filter 24 from the outer peripheral surface side to the inner peripheral surface side is described in detail.

As illustrated in FIG. 1, the blood flowing to the outer peripheral surface side of the blood cell removal filter 24 along the flow passage 29 first passes through the exterior sheet 28 (refer to FIG. 2(A)). In this process, leukocytes contained in the blood are hardly captured by the exterior sheet 28.

The blood passing through the exterior sheet 28 passes through the filter sheet 26 forming the outer peripheral surface of the wound body 25 illustrated in FIG. 4. In this process, a larger number of leukocytes contained in the blood are captured by the filter sheet 26 than the number of leukocytes captured when the blood passing through the exterior sheet 28. The blood passing through the exterior sheet 28 partially passes through the filter through-holes 39 formed in the filter sheet 26 forming the outer peripheral surface of the wound body 25 without leukocytes being captured.

The blood passing through the filter sheet 26 forming the outer peripheral surface of the wound body 25 or the filter through-holes 39 formed in the filter sheet 26 passes through the spacer sheet 27 adjacent to the filter sheet 26 on the inner peripheral surface side of the filter sheet 26. In this process, leukocytes contained in the blood are hardly captured by the exterior sheet 28 in the same manner as in the case where the blood passes through the exterior sheet 28.

Thereafter, the blood flows to the flow passage 30 while alternately passing through the filter sheet 26 and the spacer sheet 27. In this process, leukocytes contained in the blood are captured by the filter sheet 26 whenever the blood passes through the filter sheet 26. Since the blood is filtered by the filter sheet 26 as described above, the number of the leukocytes contained in the blood reaching the flow passage 30 becomes smaller than the number of the leukocytes before the blood is filtered by the filter sheet 26.

The filtration capability of the filter sheet 26 decreases with an increase in the accumulation amount of the blood passing through the filter sheet 26. This is because blood cell components, such as leukocytes and blood platelets, are captured by a large number of the holes formed in the filter sheet 26, so that the holes capturing the leukocytes are closed. This may cause so-called clogging in which the flow of the blood in the filter sheet 26 is blocked, so that the blood cannot pass through the filter sheet 26.

Then, the reduction in the filtration capability of the filter sheet 26 described above occurs from the outer peripheral surface side of the wound body 25. More specifically, the filtration capability of the filter sheet 26 of the outer peripheral surface of the wound body 25 decreases first.

However, even when the filtration capability of the filter sheet 26 on the outer peripheral surface of the wound body 25 decreases, the blood can flow to the inner peripheral surface side of the wound body 25 through the filter through-holes 39 formed in the filter sheet 26 on the outer peripheral surface of the wound body 25. Thus, the blood reaches the spacer sheet 27 adjacent to the filter sheet 26 on the inner peripheral surface side of the filter sheet 26. Thereafter, the blood passes through the spacer sheet 27 to reach the filter sheet 26 adjacent to the spacer sheet 27 on the inner peripheral surface side of the spacer sheet 27, i.e., the second filter sheet 26 from the outer peripheral surface of the wound body 26. Then, leukocytes contained in the blood are captured within the second filter sheet 26.

As described above, in this embodiment, even when the filtration capability of the filter sheet 26 on the outer peripheral surface of the wound body 25 decreases, a large amount of blood can reach the second filter sheet 26 from the outer peripheral surface of the wound body 26 through the filter through-holes 39 disposed throughout the outer peripheral surface of the wound body 25.

When the filtration capability of the filter sheets 26 other than the filter sheet 26 on the outer peripheral surface of the wound body 25 decrease, so that the blood cannot pass through the filter sheets 26, the blood can move from the outer peripheral surface side to the inner peripheral surface side of the wound body 25 while moving in the circumferential direction 102 of the wound body 25 along the spacer sheet 27. Moreover, since the spacer sheet 27 forms a part of the inner peripheral surface of the wound body 25 as described above, the blood can reach the internal space of the wound body 25 while moving in the circumferential direction 102 of the wound body 25 along the spacer sheet 27. More specifically, the blood can reach the flow passage 30. As described above, even when the filter sheet 26 is clogged, the blood is prevented from being completely unmovable in the wound body 25.

The pressure differences (mmHg) to the elapsed time (minute) when blood is continuously caused to flow into filter devices of Example and Comparative Example are measured. Herein, the pressure difference is the pressure loss of the blood cell removal filter 24. In Example, the filter device 20 illustrated in FIG. 1 was used and one illustrated in FIG. 4 was used as the wound body 25. In Comparative Example, the filter device 20 having a wound body different from the wound body used in Example was used. In Comparative Example, one having no filter through-holes 39 was used as the wound body.

The measurement results are shown in FIG. 9. In FIG. 9, the pressure difference of Comparative Example rapidly increases at the elapsed time of about 60 minutes as compared with the pressure difference of Example. This shows that when 60 minutes has passed, the fluidity of the blood of Comparative Example further deteriorates than the fluidity of the blood of Example. More specifically, the Example can maintain good blood fluidity over a longer period of time than Comparative Example.

[Operational Effects of this Embodiment]

According to this embodiment, the blood flowing from the outer peripheral surface side into the inner peripheral surface side of the wound body 25 can enter the filter sheet 26 on the inner peripheral surface side through the filter through-holes 39 formed in the filter sheet 26. Thus, the use efficiency of the filter sheet 26 can be increased.

Moreover, by providing the filter through-holes 39 in a wide range of the outer peripheral surface of the wound body 25, entry routes through which the blood enters the filter sheet 26 on the inner peripheral surface side can be increased.

Moreover, when the filtration is performed, the blood can enter not only the filter sheet 26 on the outer peripheral surface side but the filter sheet 26 on the inner peripheral surface side through the filter through-holes 39, and therefore the volume of the filter sheet 26 which the blood can enter can be increased. Thus, the size of the filter device 20 can be reduced in the axial direction 101 of the wound body 25 while maintaining the filtration capability equal to the filtration capability of a former filter device 20 having no filter through-holes 39.

Moreover, the surface area on the outer peripheral surface side of the wound body 25 is larger than the surface area on the inner peripheral surface side thereof, which is desirable because the filter sheet 26 on the outer peripheral surface side of the wound body 25 can be efficiently utilized. According to this embodiment, blood can enter the filter sheet 26 on the inner peripheral surface side by one turn relative to the filter sheet 26 on the outer peripheral surface side in the radial direction of the wound body 25 through the filter through-holes 39 formed in the filter sheet 26 of the outer peripheral surface. Therefore, the filter sheet 26 on the outer peripheral surface of the wound body 25 having a large surface area and the filter sheet 26 on the inner side by one turn relative to the outer peripheral surface can be utilized.

Moreover, according to this embodiment, since the filter sheet 26 is disposed on both the back-and-front surface sides of the spacer sheet 27, the proportion of the filter sheet 26 in the wound body 25 can be increased. Moreover, since the spacer sheet 27 is caused to abut on the filter sheet 26 on both surfaces, the deviation of the spacer sheet 27 to the filter sheet 26 can be reduced.

Moreover, according to this embodiment, even when the situation that the filter sheet 26 is clogged, so that the blood cannot enter the filter sheet 26 occurs, the blood can reach the inner peripheral surface of the wound body through the spacer sheet 27 from the filter through-holes 39 formed in the filter sheet 26 on the outer peripheral surface. Thus, the occurrence of the situation that the blood cannot pass through the wound body 25 can be prevented.

[Modification 1]

In the embodiment described above, although the filter through-holes 39 are formed only on one side (upper side relative to the fold in FIG. 2(B)) with respect to the fold in the spacer sheet 27, the filter through-holes 39 may be formed in both sides with respect to the fold in the spacer sheet 27.

[Modification 2]

In the embodiment described above, although the filter through-holes 39 are formed only in the outer peripheral surface of the wound body 25 as illustrated in FIG. 4, the filter through-holes 39 may be formed also in the peripheral surfaces other than the outer peripheral surface of the wound body 25.

For example, as illustrated in FIG. 5 and FIG. 6, the filter through-holes 39 may be formed in the outer peripheral surface of the wound body 25 and the second peripheral surface from the outer peripheral surface. In FIG. 5, the filter through-holes 39 formed in the second peripheral surface from the outer peripheral surface are illustrated by the dotted lines. In this case, filter through-holes 39A formed in the outer peripheral surface of the wound body 25 and filter through-holes 39B formed in the second peripheral surface from the outer peripheral surface of the wound body 25 are desirably disposed at different positions in at least one of the circumferential direction 102 or the axial direction 101. More specifically, it is desirable that the filter through-holes 39A formed in the outer peripheral surface of the wound body 25 and the filter through-holes 39B formed in the second peripheral surface from the outer peripheral surface of the wound body 25 are disposed at positions which are not overlapped.

FIG. 5(A) and FIG. 6 illustrate an example in which the filter through-holes 39A formed in the outer peripheral surface of the wound body 25 and the filter through-holes 39B formed in the second circumferential side from the outer peripheral surface of the wound body 25 are disposed at different positions in the circumferential direction 102 and at the same positions in the axial direction 101. On the other hand, FIG. 5(B) illustrates an example in which the filter through-holes 39A formed in the outer peripheral surface of the wound body 25 and the filter through-holes 39B formed in the second peripheral surface from the outer peripheral surface of the wound body 25 are disposed at different positions both in the circumferential direction 102 and in the axial direction 101.

The filter through-holes 39 may be formed also in peripheral surfaces other than the outer peripheral surface and the second peripheral surface from the outer peripheral surface. In this case, the filter through-holes 39 of the filter sheet 26 are desirably disposed at positions which are not overlapped with the other filter through-holes 39 formed in the peripheral surface on the outer peripheral surface side by one turn and on the inner peripheral surface side by one turn in the radial direction of the wound body 25 relative to the filter through-holes 39.

According to the modification 2, when the blood flows from the outer peripheral surface side to the inner peripheral surface side of the wound body 25 along the radial direction of the wound body 25, for example, the blood flowing into the filter sheet 26 on the inner peripheral surface side by one turn through the filter through-holes 39 formed in the filter sheet 26 of a certain peripheral surface reaches regions which are not the filter through-holes 39 of the filter sheet 26 to enter the filter sheet 26. More specifically, by not overlapping the filter through-holes 39 as in the configuration described above, the surface area of the filter sheet 26 which blood can enter can be enlarged. Thus, the use efficiency of the filter sheet 26 can be increased.

[Modification 3]

As illustrated in FIG. 10(A), spacer through-holes 40 may be formed in the spacer sheet 27. The number of the spacer through-holes 40 may be one or two or more.

The spacer through-holes 40 are formed at positions superimposed on the filter through-holes 39. Herein, the "superimpose" has the following meaning. More specifically, the spacer through-holes 40 are formed on the inner peripheral side or the outer peripheral side by one turn in the radial direction relative to the filter through-holes 39 and formed in such a manner that the spacer through-holes 40 are at least partially located at the same positions both in the axial direction 101 and in the circumferential direction 102 as the positions of the filter through-holes 39.

It is preferable for the spacer through-holes 40 formed on the inner peripheral side by one turn relative to the filter through-holes 39 located on the outer peripheral surface to completely contain the filter through-holes 39 located on the outer peripheral surface thereinside when viewed along the radial direction. However, the spacer through-holes 40 formed on the inner peripheral side by one turn relative to the filter through-holes 39 located on the outer peripheral surface may be completely in agreement with the filter through-holes 39 located on the outer peripheral surface when viewed along the radial direction. Alternatively, the spacer through-holes 40 formed on the inner peripheral side by one turn relative to the filter through-holes 39 located on the outer peripheral surface may be only partially overlapped with the filter through-holes 39 located on the outer peripheral surface when viewed along the radial direction.

In the wound body 25 illustrated in FIG. 10(B) in which the filter sheet 26 and the spacer sheet 27 of the configuration illustrated in FIG. 10(A) are wound, the spacer through-holes 40 formed on the inner peripheral side by one turn relative to the filter through-holes 39 located on the outer peripheral surface are larger than the filter through-holes 39 located on the outer peripheral surface.

Herein, the size of the spacer through-holes 40 and the filter through-holes 39 is the size along the peripheral surface of the wound body 25 and is not the length (depth of each of the through-holes 40 and 39) along the radial direction of the wound body 25. The fact that the spacer through-holes 40 are larger than the filter through-holes 39 means that, when the center of the filter through-hole 39 is aligned with the position of any one of the spacer through-holes 40, the filter through-hole 39 is completely contained in a region inside the spacer through-hole 40.

In this case, when the spacer through-holes 40 and the filter through-holes 39 have a circular shape, for example, the diameter of the spacer through-holes 40 is equal to or larger than the diameter of the filter through-holes 39. When the spacer through-holes 40 and the filter through-holes 39 have an oval shape, the major axis of the spacer through-holes 40 is equal to or larger than the major axis of the filter through-holes 39 and the minor axis of the spacer through-holes 40 is equal to or larger the minor axis of the filter through-holes 39. When the spacer through-holes 40 and the filter through-holes 39 have a rectangular shape, the length of the longer side of the spacer through-holes 40 is equal to or larger than the length of the longer side of the filter through-holes 39 and the length of the shorter side of the spacer through-holes 40 is equal to or larger than the length of the shorter side of the filter through-holes 39.

In the wound body 25 illustrated in FIG. 10(B), the filter through-holes 39 and the spacer through-holes 40 form concave portions, which are deeper than those illustrated in FIG. 4, on the outermost periphery of the wound body 25. The bottom surface of the concave portions is the filter sheet 26 formed on the inner peripheral surface side relative to the outer peripheral surface of the wound body 25. More specifically, one exposed to the outside through the concave portions is the filter sheet 26.

According to the modification 3, when the inner peripheral surface side is viewed through the filter through-holes 39 formed in the filter sheet 26 on the outer peripheral surface, the filter sheet 26 on the inner peripheral surface side is exposed through the filter through-holes 39 and the spacer through-holes 40 superimposed on the filter through-hole 39. Therefore, blood can flow into the filter sheet 26 on the inner peripheral surface side through the filter through-holes 39 and the spacer through-holes 40 formed in the wound body 25 without passing through the spacer sheet 27.

Moreover, according to the modification 3, the spacer through-holes 40 on the inner peripheral side by one turn relative to the filter through-holes 39 located on the outer peripheral surface are larger than the filter through-holes 39 located on the outer peripheral surface. Therefore, even when the positions in the circumferential direction of the filter through-holes 39 and the spacer through-holes 40 are deviated from each other by winding the filter sheet 26 and the spacer sheet 27, a possibility that the superposition in the circumferential direction of both the through-holes can be maintained can be made high.

[Modification 4]

In the embodiments described above, although the wound body 25 is formed by spirally winding one in which the spacer sheet 27 is sandwiched between the filter sheet 26 folded in half but the configuration of the wound body 25 is not limited to such a configuration. For example, the wound body 25 may be formed as illustrated in FIG. 8 by spirally winding one in which one filter sheet 26 and one spacer sheet 27 are laminated (refer to FIG. 7(A)) in such a manner that the filter sheet 26 is located on the outer peripheral surface side in the radial direction.

The wound body 25 may be formed by spirally winding one in which the spacer sheet 27 is sandwiched between two filter sheets 26, for example (refer to FIG. 7(B)). In this case, the two filter sheets 26 are disposed in the state where one side (right side in FIG. 7(B)) extends beyond the spacer sheet 27 as illustrated in FIG. 7(B). The wound body 25 is formed by spirally winding the same in such a manner that the one side is located on the outer peripheral surface side.

When the wound body 25 is formed by spirally winding one in which the spacer sheet 27 is sandwiched between two filter sheets 26, one of the two filter sheets 26 (the filter sheet 26 on the lower side in FIG. 7(C)) may be disposed in the state where one side (right side in FIG. 7(C)) does not extend beyond the spacer sheet 27 as illustrated in FIG. 7(C). In this case, the wound body 25 is formed by spirally winding the same in such a manner that a longer one of the two filter sheets 26, i.e., the filter sheet disposed in such a manner that one side extends beyond the spacer sheet 27, is located on the outside in the radial direction.

Also in the configuration in which the spacer through-holes 40 are formed in the spacer sheet 27, i.e., the configuration of the modification 3, the wound body 25 may be configured as illustrated in FIG. 11(B) by spirally winding one in which one filter sheet 26 and one spacer sheet 27 are laminated (refer to FIG. 11(A)) in such a manner that the filter sheet 26 is located on the outer peripheral surface side in the radial direction.

[Modification 5]

In the embodiments described above, although the spacer sheet 27 forms at least one part of the inner peripheral surface of the wound body 25, the filter sheet 26 may form the entire inner peripheral surface of the wound body 25 as illustrated in FIG. 10 and FIG. 11.

In this case, blood needs to pass through the filter sheet 26 forming the inner peripheral surface in order to reach the internal space of the wound body 25. When the filter sheet 26 forming the inner peripheral surface is clogged, the blood cannot reach the internal space of the wound body 25. However, by increasing the number of turns of the wound body 25, a possibility that the filter sheet 26 forming the inner peripheral surface is clogged can be made low.

[Modification 6]

As described above, when the number of turns of the wound body 25 is increased in the modification 5, a possibility that the filter sheet 26 forming the inner peripheral surface is clogged can be made low but the possibility cannot be reduced to zero. There is a case where the number of turns of the wound body 25 cannot be increased, such as a case where the size of the wound body 25 is to be reduced, for example.

In the case described above, this modification 6 is effective. In the wound body 25 in the modification 6, the filter sheet 26 forms the entire inner peripheral surface of the wound body 25 as illustrated in FIG. 12 as in the wound body 25 in the modification 5. In the wound body 25 in the modification 6, the filter through-holes 39 and the spacer through-holes 40, which are formed in the modification 3, are formed in not only a portion forming the outer peripheral surface of the wound body 25 but a portion forming the inner peripheral surface thereof in the filter sheet 26. More specifically, the wound body 25 is one in which the filter sheet 26 is wound in a spiral shape in such a manner that the filter through-holes 39 are located on the outer peripheral surface and the inner peripheral surface.

In the wound body 25 illustrated in FIG. 12, the spacer through-holes 40 on the outer peripheral side by one turn relative to the filter through-holes 39 located on the inner peripheral surface are superimposed on the filter through-holes 39 located on the inner peripheral surface and are larger than the filter through-holes 39 located on the inner peripheral surface. Herein, the "superpose" and the "large" have the same meanings as the meanings described in the modification 3.

According to the modification 6, even when the portion forming the inner peripheral surface of the wound body 25 in the filter sheet 26 is clogged, blood can pass through the inner peripheral surface through the filter through-holes 39 and the spacer through-holes 40 formed in the portion.

According to the modification 6, the spacer through-holes 40 on the outer peripheral side by one turn relative to the filter through-holes 39 located on the inner peripheral surface are larger than the filter through-holes 39 located on the inner peripheral surface. Therefore, even when the positions in the circumferential direction of the filter through-holes 39 and the spacer through-holes 40 are deviated from each other by winding the filter sheet 26 and the spacer sheet 40 as in the modification 3, a possibility that the superposition in the circumferential direction of both through-holes can be maintained can be made high.

[Second Embodiment]

A blood treatment filter device 100 in this embodiment at least has a filter device 20, a first blood circuit 131 and a second blood circuit 132, a first bypass circuit 133 and a second bypass circuit 134, and four valves 141, 142, 143, and 144 as illustrated in FIG. 13 and FIG. 14. Furthermore, the blood treatment filter device 100 in this embodiment may further have a pump 151, a pressure sensor 152, a chamber 153, and a controller 154 illustrated in FIG. 13.

The filter device 20 is configured by a cylindrical-shaped body container 21 having internal space and a blood cell removal filter 24 which is placed in the internal space of the body container 21 as described in the first embodiment. The filter device 20 is a device which performs blood treatment of filtering specific components (typically leukocytes) from blood supplied through the first blood circuit 131, and then discharging the filtered blood to the second blood circuit 132. Prior to the blood treatment, priming treatment of removing air and the like in the filter device 20 is performed. The details of the priming treatment and the blood treatment are described later.

The body container 21 is formed with a thermoplastic resin, such as polycarbonate, for example. The body container 21 has a first port 22 and a second port 23 which are continuous to the internal space as illustrated in FIG. 13. The first port 22 is provided on the end surface of one side of the body container 21 and is connected to the first blood circuit 131. The second port 23 is provided on the end surface of the other side of the body container 21 and is connected to the second blood circuit 132. The body container 21 during the use of the blood treatment filter device 100 is disposed with the first port 22 located above the second port 23 in the gravity direction.

The blood cell removal filter 24 is formed by a filter sheet 26 wound in a cylindrical shape, a cylindrical-shaped exterior sheet 28 covering the outer peripheral surface of the filter sheet 26, and seals 31 provided at both end portions in the axial direction. More specifically, the blood cell removal filter 24 presents a cylindrical shape as a whole. A spacer sheet 27 may be provided between the wound filter sheet 26. However, the specific configuration of the blood cell removal filter 24 is not limited thereto in the second embodiment. For example, the blood cell removal filter 24 may be configured only by the filter sheet 26 and filter through-holes 39 or spacer through-holes 40 described later may not be always provided.

The filter sheet 26 is formed with a porous material which adsorbs specific components among the components forming blood and, for example, nonwoven fabric containing polyester, polypropylene, polyethylene terephthalate, polytetrafluoroethylene, and the like is mentioned. These materials may be subjected to various kinds of surface treatment for controlling the blood cell component permeability for use. For example, these materials may be subjected to hydrophilization treatment for use. The average pore size of the filter sheet 26 containing the porous material is preferably set to be large in such a manner as not to impair the blood fluidity and not to increase the pressure loss of the filter and to be small in such a manner as to be able to secure a moderate leukocyte removal ratio.

The spacer sheet 27 is a net-like sheet. The average pore size of the spacer sheet 27 is desirably set to be larger than the average pore size of the filter sheet 26. Thus, the specific components described above are easier to pass through the spacer sheet 27 than through the filter sheet 26.

The filter sheet 26 is formed by sandwiching the spacer sheet 27 between the filter sheet 26 folded in half. Then, the filter sheet 26 is formed into a cylindrical shape by being spirally wound with an open side end portion 26A of the filter sheet 26 located on the inside and with a fold side end portion 26B located on the outside. In the filter sheet 26, the length of each of one side and the other side of the fold side end portion 26B is longer than that of the spacer sheet 27. As a result, the outermost peripheral surface and the innermost peripheral surface of the filter sheet 26 wound in the cylindrical shape are covered with the filter sheet 26.

The filter through-holes 39 are formed in the filter sheet 26. The filter through-holes 39 are formed at equidistant positions from the fold side end portion 26B on one side and the other side of the fold side end portion 26B. Moreover, the spacer sheet 27 has the spacer through-holes 40 at the positions corresponding to the filter through-holes 39 of the filter sheet 26. More specifically, the corresponding through-holes 30 and 40 are caused to communicate with each other in the filter sheet 26 wound in the cylindrical shape. The diameter of the spacer through-holes 40 in this embodiment is larger than the diameter of the filter through-holes 39. In the filter sheet 26 wound in the cylindrical shape, the filter through-holes 39 are disposed at positions included in the corresponding spacer through-holes 40. As a result, the spacer sheet 27 is not exposed to the outermost peripheral surface of the filter sheet 26 wound in the cylindrical shape.

The filter through-holes 39 and the spacer through-holes 40 in this embodiment are formed at the positions forming the outermost peripheral surface of the filter sheet 26 wound in the cylindrical shape. The filter through-holes 39 and the spacer through-holes 40 in this embodiment are formed at a plurality of positions spaced from each other in the circumferential direction 102 of the filter sheet 26 wound in the cylindrical shape. The filter through-holes 39 and the spacer through-holes 40 may be formed at a plurality of positions spaced from each other in the axial direction 101 of the filter sheet 26. Furthermore, the filter through-holes 39 and the spacer through-holes 40 may be formed at positions forming the innermost peripheral surface of the filter sheet 26 wound in the cylindrical shape. However, the positions where the filter through-holes 39 and the spacer through-holes 40 are formed are not limited thereto.

The exterior sheet 28 is a net-like sheet formed with a material harder than the filter sheet 26. The exterior sheet 28 is a tricot material obtained by knitting fibers, for example. The average pore size of the exterior sheet 28 is desirably set to be larger than the average pore size of the filter sheet 26. The exterior sheet 28 is formed into a cylindrical shape having an outer diameter size larger than the outer diameter size of the filter sheet 26 and holds the filter sheet 26 thereinside. By attaching the fold side end portion 26B of the filter sheet 26 to the inner peripheral surface of the exterior sheet 28, the shape of the filter sheet 26 is maintained. The blood cell removal filter 24 in an unused state (in other words, a state before priming treatment is performed) is in a dry state where liquid is not contained. More specifically, the internal space of the body container 21 in the unused state is filled with air or the like.

The seals 31 are provided at both end portions in the axial direction of the blood cell removal filter 24. The seals 31 do not allow the passage of liquid by being hardened by an adhesive or the like. More specifically, the seals 31 seal both end portions in the axial direction of the blood cell removal filter 24 in a fluid-tight manner. The seals 31 are not limited to the structure in which the seals 31 are hardened by an adhesive or the like insofar as both the end portions in the axial direction of the blood cell removal filter 24 can be sealed in a fluid-tight manner. For example, the seals 31 may be members formed with rubber or the like which do not allow the passage of liquid. A through-hole 33 is formed in the central portion of the seal provided at a lower end portion of the blood cell removal filter 24. With respect to the through-hole 33, the inside and the outside of the blood cell removal filter 24 are caused to communicate with each other through the through-hole 33.

The blood cell removal filter 24 is attached to the wall surface (wall surface serving as the bottom surface during use) of the body container 21 in which the second port 23 is formed. The length in the axial direction 101 (length along the vertical direction in FIG. 1) of the blood cell removal filter 24 is shorter than the length in the axial direction 101 of the internal space of the body container 21. The outer diameter size of the blood cell removal filter 24 is smaller than the internal diameter size (i.e., diameter of the internal space) of the body container 21. As a result, a gap is formed between the wall surface (wall surface serving as the top surface during use) of the body container 21 in which the first port 22 is formed and the blood cell removal filter 24 and a gap is formed between the inner peripheral surface of the body container 21 and the outer peripheral surface of the blood cell removal filter 24. The gaps serve as a flow passage 29 leading to the first port 22. More specifically, in the body container 21, the first port 22 and the internal space on the outer peripheral surface side of the blood cell removal filter 24 are continuous to each other by the flow passage 29. The internal space of the cylindrical-shaped blood cell removal filter 24 is continuous to the second port 23 through the through-hole 33. The internal space of the blood cell removal filter 24 serves as a flow passage 30 leading to the second port 23. More specifically, the internal space on the inner peripheral surface side of the blood cell removal filter 24 and the second port 23 are continuous to each other by the flow passage 30 in the body container 21.

In the first blood circuit 13, one end is connected to a container 155 (refer to FIG. 13) charged with a priming liquid or a patient (refer to FIG. 14) and the other end is connected to the first port 22 of the filter device 20 as illustrated in FIG. 13 and FIG. 14. The first blood circuit 131 is provided with the pump 151, the pressure sensor 152, and the chamber 153 on the way to the filter device 20. The pump 151 supplies a priming liquid or blood (hereinafter referred to as "liquid") to the filter device 20 through the first blood circuit 131. The pressure sensor 152 measures the pressure of the liquid flowing through the first blood circuit 131. The chamber 153 is an air reservoir collecting air bubbles mixed in the liquid flowing through the first blood circuit 131. The controller 154 controls the drive of the pump 151 and collects the pressure values measured by the pressure sensor 152. The pressure sensor 152 may measure the pressure of the liquid at the position of the chamber 153, and then output the measured pressure values to the controller 154.

In the second blood circuit 132, one end is connected to the second port 23 of the filter device 20 and the other end is connected to a waste liquid tank 156 (refer to FIG. 13) or a patient (refer to FIG. 14) as illustrated in FIG. 13 and FIG. 14. Although not illustrated, a pressure sensor and a chamber may be provided on the way to the waste liquid tank 156 from the filter device 20 of the second blood circuit 132.

The first bypass circuit 133 and the second bypass circuit 134 are flow passages which guide the liquid flowing through the first blood circuit 131 to the second blood circuit 132 without passing through the filter device 20. In detail, the first bypass circuit 133 is connected to the first blood circuit 131 at a connection position 135 and is connected to the second blood circuit 132 at a connection position 136. The second bypass circuit 134 is connected to the first blood circuit 131 at a connection position 137 and is connected to the second blood circuit 132 at a connection position 138. In the first blood circuit 131, the connection position 137 is located closer to the first port 22 than the connection position 135. In the second blood circuit 132, the connection position 138 is located further from the second port 23 than the connection position 136.

The valve 141 is provided in the first blood circuit 131 between the connection positions 135 and 37. More specifically, the valve 141 permits or regulates the flow of the liquid in the first blood circuit 131 (i.e., opens/closes the first blood circuit 131) between the connection positions 135 and 37. The valve 142 is provided in the second blood circuit 132 between the connection positions 136 and 38. More specifically, the valve 142 permits or regulates the flow of the liquid in the second blood circuit 132 (i.e., opens/closes the second blood circuit 132) between the connection positions 136 and 38. The valve 143 is provided in the first bypass circuit 133 and permits or regulates the flow of the liquid in the first bypass circuit 133 (i.e., opens/closes the first bypass circuit 133). The valve 144 is provided in the second bypass circuit 134 and permits or regulates the flow of the liquid in the second bypass circuit 134 (i.e., opens/closes the second bypass circuit 134).

Next, the priming treatment to the blood treatment filter device 100 in this embodiment is described with reference to FIG. 13. First, the valves 141 and 142 are closed and the valves 143 and 144 are opened. Thus, the flow of the priming liquid in the first blood circuit 131 is regulated between the connection positions 135 and 137, the flow of the priming liquid in the second blood circuit 132 is regulated between the connection positions 136 and 138, and then the flow of the priming liquid in the first bypass circuit 133 and the second bypass circuit 134 is permitted. Next, by driving the pump 151 under the control by the controller 154, the priming liquid is caused to flow out of the container 155 into the first blood circuit 131. The container 155 is charged with the priming liquid having the quantity which exceeds the internal volume of the filter device 20, the first blood circuit 131, the second blood circuit 132, the first bypass circuit 133, and the second bypass circuit 134.

Thus, the priming liquid flowing into the first blood circuit 131 flows toward the closed valve 141 while pressing out air and the like in the first blood circuit 131, and then flows into the first bypass circuit 133 at the connection position 135. The priming liquid flowing into the first bypass circuit 133 flows into the second blood circuit 132 through the connection position 136 while pressing out air and the like in the first bypass circuit 133. Furthermore, the priming liquid flowing into the second blood circuit 132 flows into the filter device 20 through the second port 23 while pressing out air and the like between the closed valve 142 and the second port 23.

The priming liquid flowing into the internal space of the filter device 20 through the second port 23 is accumulated on a lower portion of the internal space of the body container 21 while entering pores of the blood cell removal filter 24, so that the liquid surface gradually rises with the progress of time. Thus, air and the like present in the internal space of the body container 21 are discharged through the first port 22. The priming liquid filling the internal space of the body container 21 flows out to the first blood circuit 131 through the first port 22. The priming liquid flowing into the first blood circuit 131 flows into the second bypass circuit 134 through the connection position 137 while pressing out air and the like between the first port 22 and the closed valve 141, flows into the second blood circuit 132 through the connection position 138 while pressing out air and the like in the second bypass circuit 134, and then is discharged into the waste liquid tank 156 while pressing out air and the like between the valve 142 and the waste liquid tank 156.

Due to the fact that the priming liquid is discharged into the waste liquid tank 156 through the second blood circuit 132, air and the like are removed from the inside of the blood treatment filter device 100. Then, the pump 151 is stopped under the control by the controller 154, whereby the priming treatment to the blood treatment filter device 100 is completed. More specifically, the blood treatment filter device 100 after the priming treatment is completed, the internal space (internal space of the body container 21, the first blood circuit 131, the second blood circuit 132, the first bypass circuit 133, and the second bypass circuit 134) is filled with the priming liquid.

Next, blood treatment employing the blood treatment filter device 100 in this embodiment is described with reference to FIG. 14. First, in the blood treatment filter device 100 in the state where the above-described priming treatment is performed (i.e., the internal space is filled with the priming liquid), the valves 141 and 142 are opened and the valves 143 and 144 are closed. Thus, the flow of the blood from the first blood circuit 131 to the first port 22 is permitted, the flow of the blood from the second port 23 to the second blood circuit 132 is permitted, and the flow of the blood in the first bypass circuit 133 and the second bypass circuit 134 is regulated. Next, by driving the pump 151 under the control by the controller 154, the blood is caused to flow out of a patient into the first blood circuit 131.

The blood which flows into the internal space of the body container 21 through the first port 22 from the first blood circuit 131 flows to the outer peripheral surface side of the blood cell removal filter 24 along the flow passage 29 to pass through the blood cell removal filter 24 from the outer peripheral surface side to the inner peripheral surface side (i.e., inwardly in the radial direction) as illustrated in FIG. 1. In this process, leukocytes contained in the blood are captured by the blood cell removal filter 24 (mainly filter sheet 26). Furthermore, the blood from which leukocytes are filtered flows out of the flow passage 30 into the second blood circuit 132 through the second port 23, and then returned to a patient. In FIG. 1, the blood flow in the flow passages 29 and 30 is indicated by the arrow and the blood flow in the blood cell removal filter 24 is indicated by the white arrow.

The controller 154 monitors the pressure values measured by the pressure sensor 152 during the execution of the blood filter treatment. Then, when the pressure value exceeds a threshold value, the controller 154 performs the following treatment, for example. The case where the pressure value measured by the pressure sensor 152 exceeds a threshold value shows that the blood cell removal filter 24 is clogged, so that the blood flow in the blood treatment filter device 100 is stagnant. Then, the controller 154 may open at least one of the valves 143 and 144. Thus, the blood is returned to a patient without passing through the filter device 20. The controller 154 may report abnormalities to an administrator. A specific report method is not particularly limited and a beep sound may be output or a warning may be displayed on a management terminal.

[Operational Effects of this Embodiment]

According to this embodiment, when the priming treatment is performed, the valves 141 and 142 may be closed and the valves 143 and 144 may be opened and when the blood filter treatment is performed, the valves 141 and 142 may be opened and the valves 143 and 144 may be closed. More specifically, the priming treatment and the blood treatment can be easily performed only by switching the state of the valves 141 to 144 without switching the drive direction and the like of the pump 151.

According to this embodiment, the priming liquid is caused to flow into the body container 21 from the second port 23. Thus, in the priming treatment, the internal space of the body container 21 is gradually filled with the priming liquid from the lower side in the gravity direction, so that the liquid surface gradually increases with the progress of time. Thus, air and the like present in the internal space of the body container 21 can be certainly discharged from the first port 22.

Furthermore, according to this embodiment, the blood flowing into the internal space of the body container 21 in the blood treatment passes through the blood cell removal filter 24 from the outer peripheral surface side to the inner peripheral surface side. Thus, components having a relatively large size (impurities and the like) in the blood are first filtered by the exterior sheet 28. Thus, by filtering first the blood flowing into the body container 21 by the exterior sheet 28, the clogging of the filter sheet 26 caused by the large-sized components can be suppressed.

Next, according to this embodiment, by causing blood to pass through the blood cell removal filter 24 from the outer peripheral surface side to the inner peripheral surface side, leukocytes contained in the blood are filtered by the filter sheet 26. Thus, the contact surface of the blood in the state where a large number of leukocytes are contained before being filtered and the blood cell removal filter 24 can be enlarged. Then, due to the fact that the blood flows to the inside in the radial direction of the blood cell removal filter 24, the contact surface of the blood in which the filtration of leukocytes is advanced and the blood cell removal filter 24 becomes gradually small. As a result, the clogging speed is equalized in the entire region of the filter sheet 26, and therefore the filter sheet 26 can be prevented from being unusable due to the concentration of the clogging on a part of the filter sheet 26.

Moreover, according to this embodiment, the filter sheet 26 and the spacer sheet 27 are overlapped to form the wound body 25, and therefore, a gap is formed between the filter sheets 26 adjacent to each other in the radial direction in the spirally wound filter sheet 26. Moreover, the average pore size of the spacer sheet 27 is made larger than the average pore size of the wound body 25, and therefore, even when clogging of the filter sheet 26 is advanced, the blood can be caused to smoothly flow without passing through the clogged portion.

Furthermore, according to this embodiment, the blood flows to the inner peripheral surface side of the blood cell removal filter 24 through the filter through-holes 39 and the spacer through-holes 40 formed in the filter sheet 26 and the spacer sheet 27. Thus, even when the clogging of the filter sheet 26 is advanced, the blood can be caused to smoothly flow without passing through the clogged portion.

This embodiment describes the example of permitting or regulating the flow of the liquid in each circuit by providing the valves 141 to 144 in the first blood circuit 131, the second blood circuit 132, the first bypass circuit 133, and the second bypass circuit 134, respectively. However, the present invention is not limited thereto and a clamp and the like may be used in place of the valves 141 to 144. More specifically, a specific structure of the "valve" in the present invention is not particularly limited insofar as the flow of the liquid in each circuit can be permitted or regulated.

Moreover, this embodiment describes the example of removing leukocytes in the blood treatment. However, the present invention is not limited thereto, and other components in blood can be removed by changing the blood cell removal filter 24 as appropriate.

REFERENCE SIGNS LIST

20 Filter device
21 Body container
22 First port
23 Second port
24 Blood treatment filter
25 Wound body
26 Filter sheet
27 Spacer sheet
31 Seal
39 Filter through-hole
40 Spacer through-hole
100 Blood treatment filter device
131 First blood circuit
132 Second blood circuit
133 First bypass circuit
134 Second bypass circuit
135, 136, 137, 138 Connection position
141, 142, 143, 144 Valve

The invention claimed is:

1. A blood treatment filter device comprising:
a filter sheet that is formed of a porous material and has pores through which a specific component among components contained in blood is harder to pass than other components;
a plurality of filter through-holes in the filter sheet that are formed in a thickness direction, are different from the pores in the porous material, and are larger in diameter than the pores in the porous material, and do not block the flow of blood;
a spacer sheet through which the specific component is easier to pass than through the filter sheet;
a wound body in which the filter sheet and the spacer sheet are laminated in a radial direction and are wound in a spiral shape in such a manner that at least one of the filter through-holes is located at least on an outer peripheral surface;
seals of sealing both ends in an axial direction of the wound body in a fluid-tight manner; and
a container having an internal space accommodating the wound body and having a blood inflow port connected in such a manner that blood can flow between the blood inflow port and an outer peripheral surface side of the wound body in the internal space and a blood outlet port connected in such a manner that blood can flow between the blood outlet port and an inner peripheral surface side of the wound body in the internal space.

2. The blood treatment filter device according to claim 1, wherein the spacer sheet has a spacer through-hole superimposed on at least one of the filter through-holes.

3. The blood treatment filter device according to claim 2, wherein the spacer through-hole on an inner peripheral side by one turn relative to the filter through-hole located on the outer peripheral surface is larger than the filter through-hole located on the outer peripheral surface.

4. The blood treatment filter device according to claim 1, wherein at least one of the filter through-holes is not superimposed on other filter through-holes disposed on an outer peripheral side and the inner peripheral side by one turn of the wound body relative to the through-hole in the wound body.

5. The blood treatment filter device according to claim 1, wherein
the wound body comprising a laminated sheet spirally wound in a state where an end portion of a side opposite to a fold of the filter sheet is located on the inner peripheral surface side, and
the laminated sheet is configured so that the spacer sheet is sandwiched between the filter sheet folded in half.

6. The blood treatment filter device according to claim 1, wherein at least one part of the inner peripheral surface of the wound body is formed by the spacer sheet.

7. The blood treatment filter device according to claim 2, wherein
the inner peripheral surface of the wound body is formed by the filter sheet;
the wound body is a spirally wound one in such a manner that at least one of the filter through-holes is also located on the inner peripheral surface; and
the spacer through-hole located on the outer peripheral side by one turn relative to the inner peripheral surface is larger than the filter through-hole located on the inner peripheral surface.

8. A priming method for a blood treatment filter device having:
a body container which has a first port and a second port which are continuous to an internal space and which is disposed with the first port located above the second port in a gravity direction;
a blood treatment filter that is in a dry state within the internal space of the body container and has 1) a filter sheet that is formed of a porous material, has pores through which a specific component among components contained in blood is harder to pass than other components, and has a plurality of filter through-holes that are formed in a thickness direction, are different from the pores in the porous material, and are larger in diameter than the pores in the porous material and do not block the flow of blood; 2) a spacer sheet through which the specific component is easier to pass than through the filter sheet; 3) a wound body in which the filter sheet and the spacer sheet are laminated in a radial direction and are wound in a spiral shape in such a manner that at least one of the filter through-holes is located at least on an outer peripheral surface; and 4) seals that seal both ends in an axial direction of the wound body in a fluid-tight manner;
a first blood circuit which is connected to the first port and through which liquid flows;
a second blood circuit which is connected to the second port and through which liquid flows;
a first bypass circuit which is connected to the first blood circuit and the second blood circuit and through which liquid flows; and
a second bypass circuit which is connected to a side closer to the first port relative to a connection position of the first bypass circuit in the first blood circuit and is connected to a side further from the second port relative to a connection position of the first bypass circuit in the second blood circuit and through which liquid flows,
the priming method comprising:
individually closing the circuit between a connection position of the first bypass circuit and a connection position of the second bypass circuit in each of the first blood circuit and the second blood circuit to cause a priming liquid to flow into the internal space of the body container from the first blood circuit through the first bypass circuit, the second blood circuit, and the second port, and then to cause the priming liquid to flow out of the internal space of the body container to the second blood circuit through the first port, the first blood circuit, and the second bypass circuit.

9. The priming method for the blood treatment filter device according to claim 8, wherein
the body container has a liquid flow passage which causes the first port and an internal space on an outer peripheral surface side of the cylindrical-shaped blood treatment filter to be continuous to each other and a liquid flow passage which causes an internal space on an inner peripheral surface side of the cylindrical-shaped blood treatment filter and the second port to be continuous to each other.

10. A blood treatment method employing
the priming method according to claim 8, and further comprising the step of:
closing the first bypass circuit and the second bypass circuit and individually opening the circuit between the connection position of the first bypass circuit and the connection position of the second bypass circuit in each of the first blood circuit and the second blood circuit to cause the blood to flow into the body container through the first port from the first blood circuit, and then to cause the blood to flow out to the second blood circuit through the second port from the body container.

11. A blood treatment filter device comprising:
a body container which has a first port and a second port which are continuous to an internal space and which is disposed with the first port located above the second port in a gravity direction;
a blood treatment filter that is in a dry state within the internal space of the body container and has 1) a filter sheet that is formed of a porous material, has pores through which a specific component among components contained in blood is harder to pass than other components, and has a plurality of filter through-holes that are formed in a thickness direction, are different from the pores in the porous material, and are larger in diameter than the pores in the porous material and do not block the flow of blood; 2) a spacer sheet through which the specific component is easier to pass than through the filter sheet; 3) a wound body in which the filter sheet and the spacer sheet are laminated in a radial direction and are wound in a spiral shape in such a manner that at least one of the filter through-holes is located at least on an outer peripheral surface; and 4) seals that seal both ends in an axial direction of the wound body in a fluid-tight manner;

a first blood circuit which is connected to the first port and through which liquid flows;

a second blood circuit which is connected to the second port and through which liquid flows;

a first bypass circuit which is connected to the first blood circuit and the second blood circuit and through which liquid flows;

a second bypass circuit which is connected to a side closer to the first port relative to a connection position of the first bypass circuit in the first blood circuit and is connected to a side further from the second port relative to a connection position of the first bypass circuit in the second blood circuit and through which liquid flows;

a valve which opens/closes the circuit between a connection position of the first bypass circuit and a connection position of the second bypass circuit in the first blood circuit;

a valve which opens/closes the circuit between a connection position of the first bypass circuit and a connection position of the second bypass circuit in the second blood circuit;

a valve which opens/closes the first bypass circuit; and a valve which opens/closes the second bypass circuit.

12. The blood treatment filter device according to claim 11, wherein the body container has a liquid flow passage which causes the first port and an internal space on an outer peripheral surface side of the cylindrical-shaped blood treatment filter to be continuous to each other and a liquid flow passage which causes an internal space on an inner peripheral surface side of the cylindrical-shaped blood treatment filter and the second port to be continuous to each other.

* * * * *